(12) United States Patent
Hansford et al.

(10) Patent No.: US 7,721,589 B2
(45) Date of Patent: May 25, 2010

(54) AUTOMATED SYSTEM FOR IMPACTOR TESTING

(75) Inventors: Christopher Ian Hansford, Runcorn (GB); Dominic Ewan Harvey, Runcorn (GB); Willi Juergen Kumb, Ingelheim am Rhein (DE); Anthony Michael Moran, Runcorn (GB); William Leroy Roberts, Durham, NC (US)

(73) Assignees: Glass Group Limited, Greenford, Middlesex (GB); Astech Projects Limited, Runoom, Chishire (GB); Boehringer Ingelheim International GmbH, Ingelheim (DE)

( * ) Notice: Subject to any disclaimer, the term of this patent is extended or adjusted under 35 U.S.C. 154(b) by 15 days.

(21) Appl. No.: 12/023,087

(22) Filed: Jan. 31, 2008

(65) Prior Publication Data

US 2008/0295572 A1 Dec. 4, 2008

(51) Int. Cl.
*G01N 1/00* (2006.01)
(52) U.S. Cl. .................................. 73/28.05; 73/28.04
(58) Field of Classification Search ..... 73/28.04–28.06, 73/863.22
See application file for complete search history.

(56) References Cited

U.S. PATENT DOCUMENTS

| | | | | |
|---|---|---|---|---|
| 4,321,822 A | * | 3/1982 | Marple et al. | 73/28.06 |
| 6,453,758 B1 | * | 9/2002 | Marple et al. | 73/863.22 |
| 6,723,568 B1 | * | 4/2004 | Liu et al. | 73/863.22 |
| 6,915,714 B2 | * | 7/2005 | Sanderson et al. | 73/863.22 |
| 2002/0081748 A1 | | 6/2002 | Roberts et al. | |
| 2008/0047372 A1 | * | 2/2008 | Bridge et al. | 73/863.22 |

FOREIGN PATENT DOCUMENTS

GB 2351155 A 12/2000

* cited by examiner

*Primary Examiner*—Lisa M Caputo
*Assistant Examiner*—Jonathan Dunlap
(74) *Attorney, Agent, or Firm*—James P. Riek

(57) ABSTRACT

One aspect of the invention provides an automated system for performing repeated testing using an impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages. The system comprises an impaction station for performing impaction testing using the assembled impactor; a cup manifold recovery station for recovering sample material from the impactor cups in a solvent; an impactor head cleaning station; and at least one handling system for assembling the impactor for impaction, and for subsequently disassembling the impactor and delivering the cup manifold and the impactor head to their respective stations.

18 Claims, 25 Drawing Sheets

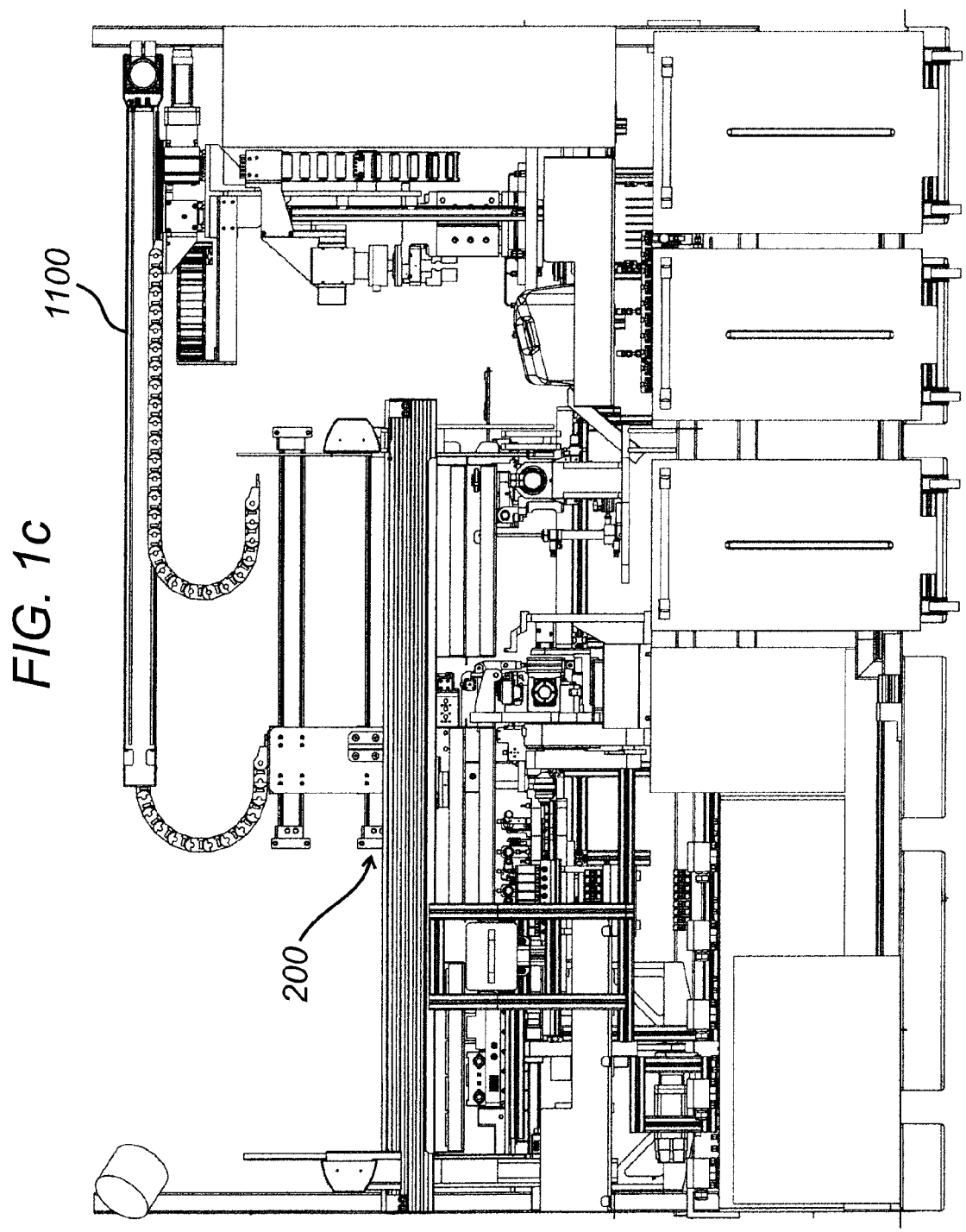

AUTOMATED SYSTEM FOR IMPACTOR TESTING

BACKGROUND TO THE INVENTION

The present invention is concerned with a system for automatically carrying out testing using a cascade impactor.

Cascade impactors are in themselves well known. They are used for analysis of aerosols, and more specifically for obtaining information about the size distribution of particles in an aerosol. Particulate material can be entrained in a gas flow to form an aerosol for analysis. The aerosol is passed through a sequence of impaction stages, larger particles tending to collect in the earlier stages and smaller particles in the later ones. In this context, the term "aerosol" is to be understood to refer to particles suspended in a fluid. The fluid in question is typically a gas although in principle it could be a liquid. The particles may be solid, liquid, or a mixture of the two.

Cascade impactors can be used for a range of purposes including for example analysis of air pollution. However, an application of particular importance in the present context involves testing of drug delivery devices such as inhalers. These are used to deliver a controlled dose of a drug to the respiratory tract of a patient. Typically the target area is the lungs, or particular areas thereof. A proportion of the dose will inevitably be retained in the mouth and throat. Inhalers are very commonly used in the treatment of asthma, but can also be used for delivery of drugs to treat other diseases, respiratory or otherwise. To demonstrate that the correct dose is being dispensed, analysis is required of particle size in the inhaler output. In a dry powder inhaler the pharmaceutical material is stored in powder form, but air drawn through the inhaler in use causes the powder to be entrained in an aerosol. There are other forms of inhaler which are relevant for present purposes including the pressurised metered dose inhaler (pMDI) in which the drug formulation comprises drug which is suspended or dissolved in a propellant (e.g. HFA 134a or HFA 227), the formulation optionally including one or more excipients, such as a surfactant. The propellant is used to create an aerosol which is then entrained in the inspiratory airflow of the patient. Nebulizer devices may also be tested using impactors of the type referred to herein. Pharmaceutical companies have a requirement to carry out batch testing on large numbers of inhalers. It is known to carry out such testing by firing the inhaler into an impactor. The powdered pharmaceutical material collects upon component parts of the impactor, from which it is then recovered for analysis. This recovery has traditionally been done by solvent rinsing in a manual process, but the labour involved is considerable and the process is slow. Hence it is highly desirable to automate impactor testing.

A form of impactor sometimes referred to as the "next generation impactor" has been developed by MSP Corporation of Minneapolis and is described for example in UK Patent 2351155. It has a tray defining multiple side-by-side impaction cups, with an impactor head to be placed upon the tray defining transfer passages from one cup to another. A nozzle plate positioned between the cup tray and the impactor head forms nozzles at the outlet of each transfer passage, the nozzles having successively smaller openings for through-passage of the aerosol, and particles with diminishing sizes are trapped in the successive impaction cups. The next generation impactor needs, after it has been dosed with one or more samples from an inhaler, to be disassembled to permit recovery of sample material from its component parts, by immersing the relevant surfaces in solvent to obtain solutions containing the sample material. This form of sample recovery is carried out on the individual cups, and also on an induction port through which the impactor interfaces with the inhaler, and in some cases on an optional preseparator used to remove the largest particles from the aerosol before it enters the impactor itself. After the recovery of the sample material, components of the impactor need to be washed and re-assembled ready for re-use.

Some details of an automation system for an impactor of this type are to be found in published United States Patent Application 2004/0250634, assignee MSP Corporation, and also in published International Patent Application WO 02/063277, applicant MSP Corporation. Both documents describe, in somewhat schematic terms, a system for carrying out repeated impaction testing automatically. However, significant technical challenges remain in practically implementing such a system.

SUMMARY OF THE INVENTION

In a first aspect, the present invention relates to an automated system for performing repeated testing using an impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the system comprising An impaction station for performing impaction testing using the assembled impactor;

a cup manifold recovery station for recovering sample material from the impactor cups in a solvent;

an impactor head cleaning station; and at least one handling system for assembling the impactor for impaction, and for subsequently disassembling the impactor and delivering the cup manifold and the impactor head to their respective stations.

The requirement for on-line cleaning of the impactor head is not recognised in the known prior art.

In a particularly preferred embodiment, the system further comprises an impactor head handling device having a movable support for carrying the impactor head between stations and an engagement device for releasably coupling the nozzle manifold to the impactor head.

Where necessary, the handling device can move the nozzle manifold and impactor head as a unit, but the releasable coupling permits the handling device to manipulate the impactor head on its own when necessary.

According to a further aspect of the present invention, there is an impaction testing arrangement comprising an impactor which has a cup manifold defining multiple impaction cups and an impactor head defining transfer passages each communicating with a respective nozzle, so that in the assembled impactor a route is defined for through-flow via the impaction cups, the nozzles and the transfer passages, the arrangement further comprising an impactor head clean up device having an exposed contact plate provided with multiple fluid outlet apertures connected to a fluid source, the fluid outlet apertures being positioned to correspond to openings of the transfer passages in the impactor head, so that when the impactor head is presented to the seal plate, fluid is able to be output into the transfer passages to clean them.

According to still a further aspect of the present invention, there is an impaction testing arrangement comprising an impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the arrangement further comprising a nozzle manifold wash module comprising upper and lower wash manifolds shaped to receive the nozzle manifold between themselves, an opening mechanism for moving at least one of the upper and lower wash manifolds with respect to the other between (a) an open configuration which permits the nozzle manifold to be introduced between them and (b) a closed configuration in which each nozzle is contained in a sealed enclosure defined between the upper and lower wash manifolds, and ports communicating with the said sealed enclosure and connectable to a fluid source for passing fluid through the sealed enclosure to carry out washing of the nozzle manifold.

In some applications, a preseparator is fitted to the impactor to remove the largest particles in the aerosol. The preseparator typically has an internal impaction cup, part-filled with liquid, to collect these large particles. After each use and clean up, the impaction cup needs to be replenished with fluid, and it is desirable to achieve this in a straightforward manner and without disassembly of the preseparator.

In accordance with still a further aspect of the present invention, there is a method of cleaning a cascade impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the method comprising separating the impactor head from the nozzle manifold and washing these components separately.

In accordance with yet another aspect of the present invention, there is an automated system for washing components of a cascade impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the system comprising an impactor head wash station, a nozzle manifold wash station, and at least one manipulation arrangement for separating the impactor head from the nozzle manifold and delivering them to their respective wash stations.

In accordance with yet a further aspect of the present invention, there is a wash station for use in an automated system for performing repeated testing using an impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the wash station being adapted to receive and clean the impactor head. Preferably, the wash station comprises a contact surface which is exposed enabling the impactor head to be placed against it, a plurality of wash fluid outlets being arranged on the contact surface to dispense wash fluid into the transfer passages. In principle, the wash station may be adapted to wash an assembly comprising both the impactor head and the nozzle manifold. Preferably however it is adapted to wash the impactor head alone.

It will be appreciated from the following detailed description that further aspects and features are comprised in the present invention.

BRIEF DESCRIPTION OF THE DRAWINGS

Specific embodiments of the present invention will now be described, by way of example only, with reference to the accompanying drawings, in which:

FIGS. 1a-d illustrate a complete system for automating impaction testing, constructed and operated in accordance with the present invention, FIG. 1a showing the system in perspective from in front and to one side, FIG. 1b showing it in plan with a supporting framework omitted, FIG. 1c being a side elevation, and FIG. 1d showing the system in perspective from the rear and to one side;

DETAILED DESCRIPTION OF THE EMBODIMENT

Figure 12A:
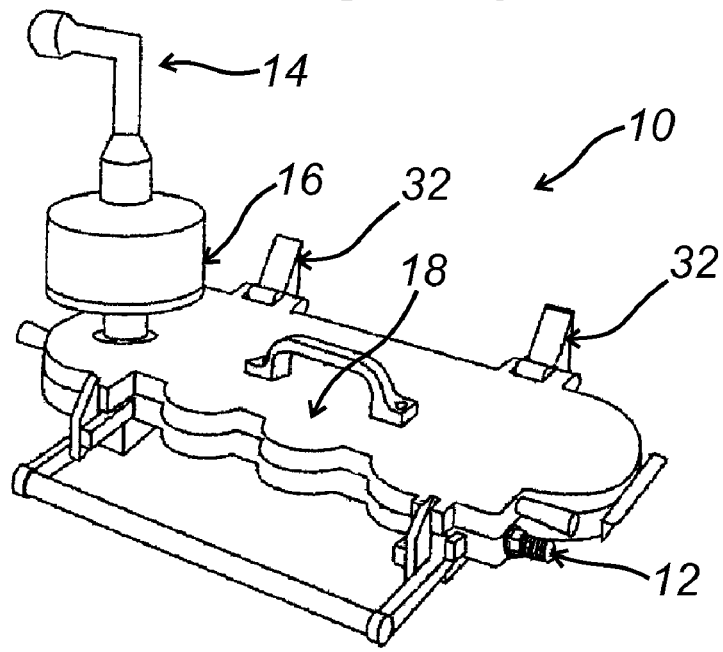
FIGS. 12a and b are perspective illustrations of a known cascade impactor, in closed and open configurations respectively.

The cascade impactor 10 illustrated in FIGS. 12a and b is a known device which is commercially available from MSP Corporation of Minneapolis. For detail about its construction, the reader is directed to UK patent 2372719 and to U.S. Pat. No. 6,453,758, the content of which is incorporated herein by reference. It is used for analysis of solid particles in aerosols, and particularly for analysis of particle size distribution. This particular impactor is intended for use in the testing of inhalers of the type used to deliver metered doses of a drug to the lungs of a patient, e.g. for the treatment of asthma. Typically, the inhaler is a dry powder inhaler (DPI) or a metered dose inhaler (pMDI), as known in the art. A vacuum applied to the impactor's exhaust 12 causes the aerosol from the inhaler to be drawn into the impactor through an induction port 14 (sometimes referred to as the "throat"), then through a preseparator 16 and through a series of impaction stages defined between an impactor head 18 and a base plate 20 carrying a cup tray 22.

The induction port 14 is an elbowed tubular component which releasably connects to the preseparator 16 through a tapered fitting, which forms the lower end of the induction port and is not seen in FIG. 1. The preseparator serves to collect the largest particles in the aerosol and is releasably mounted to the impactor head, projecting upwardly from it. The cup tray 22 is a sheet metal component defining a series of shallow, ovoid cups 24. A corresponding set of nozzles 26 is formed in a nozzle tray 28 mounted at the underside of the impactor head 18, each nozzle being arranged so that when the impactor is closed it lies over a respective cup, to direct the aerosol toward the cup. Each nozzle has numerous individual apertures, the size of the nozzle apertures becoming progressively finer in successive nozzles 26. Each nozzle communicates, through a respective transfer passage formed in the impactor head and not seen in the drawings, with a respective outlet aperture 30, each of which is arranged to lie over, and so receive the flow of aerosol from, a respective cup 24. Each transfer passage, except for the last, leads to the next nozzle 26, forming a route for passage of the aerosol through the successive impaction stages, formed by the cups 24 and nozzles 26, to the impactor exhaust 12.

Particles from the aerosol collect in the various components of the impactor, based on their particle size, whence they need to be recovered and collected for analysis in a solvent. To facilitate this, the impactor is able to be disassembled by removing the induction port 14 and preseparator 16, lifting the impactor head 18 away from the base plate 20, and removing the cup tray 22, and when necessary the nozzle tray 28. The base plate 20 and the impactor head 18 are in these drawings connected in the manner of a clam shell through hinges 32, but these—and a handle on the impactor head 18—are dispensed with in accordance with the present invention.

The testing of devices such as inhalers typically involves a large number of individual trials with the impactor. In principle the process can be carried out manually, and this has been a common practice, but the system to be described below serves to automate all of the major steps involved in use of the impactor, enabling a batch of trials to be conducted without intervention by an operator. The steps involved are:

dosing of the impactor—i.e. firing the inhaler into the impactor, causing the pharmaceutical dose to be collected in it;

dose recovery and collection from each of the relevant components of the impactor, which is done by solvent immersion of the impactor components (or at least of the relevant surfaces of the components) following its disassembly, yielding a set of solvent/pharmaceutical mixture samples (typically solutions, although in principle they could be suspensions);

clean up of the equipment. This is necessary to prevent contamination of one trial by material collected in a previous trial;

storage of the samples; and preparation of the impactor components for re-use, which includes in some procedures coating of the cups 24 and addition of a dose of solvent to an internal collection cup of the preseparator 16, after re-assembly of the impactor.

The system 100 (FIG. 1a-d) used to carry out these functions is complex. It comprises (a) modules dedicated to specific functions and (b) shared automation systems, serving demands from multiple dedicated modules. The dedicated modules comprise:

an impactor assembly, dosing and disassembly (IADDM) module 200;

a cup coating module 300;

a cup tray recovery and collection module 400;

an induction port recovery and collection module 500;

a preseparator recovery and collection module 600;

a component drying module 700; and a nozzle tray wash unit 800.

The shared automation systems comprise:

a fluid handling robot 900;

a tray handling system 1000; and an induction port and preseparator handling system 1100.

Figure 12B:
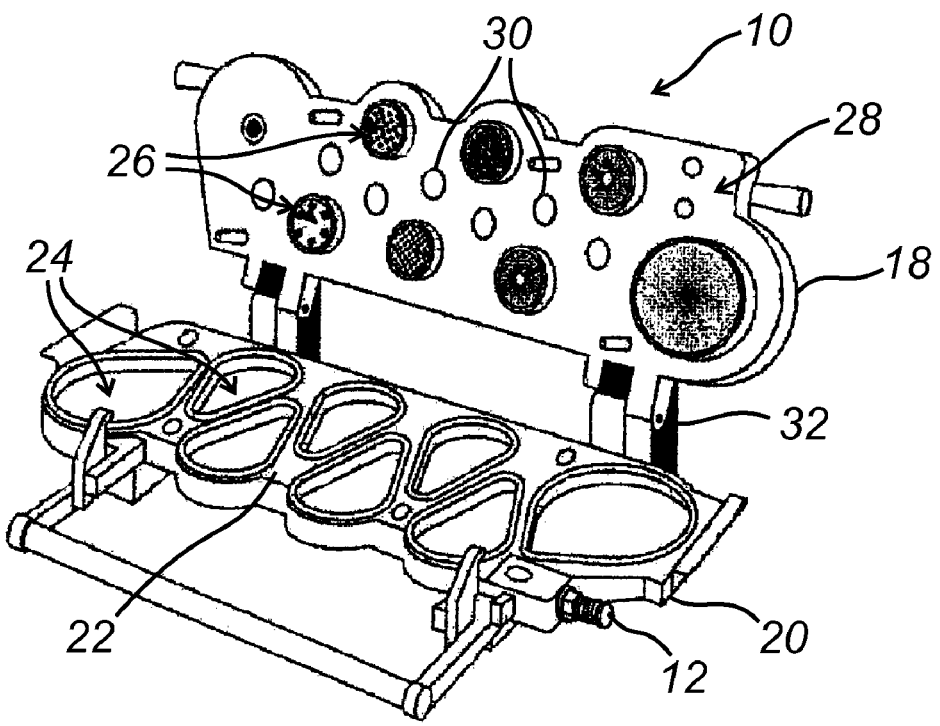

The system utilises a slightly modified version of the impactor shown in FIGS. 12a-b for effectuation of the automated processing.

Impactor Assembly, Dosing and Disassembly (IADDM) Module 200

Figure 2A:
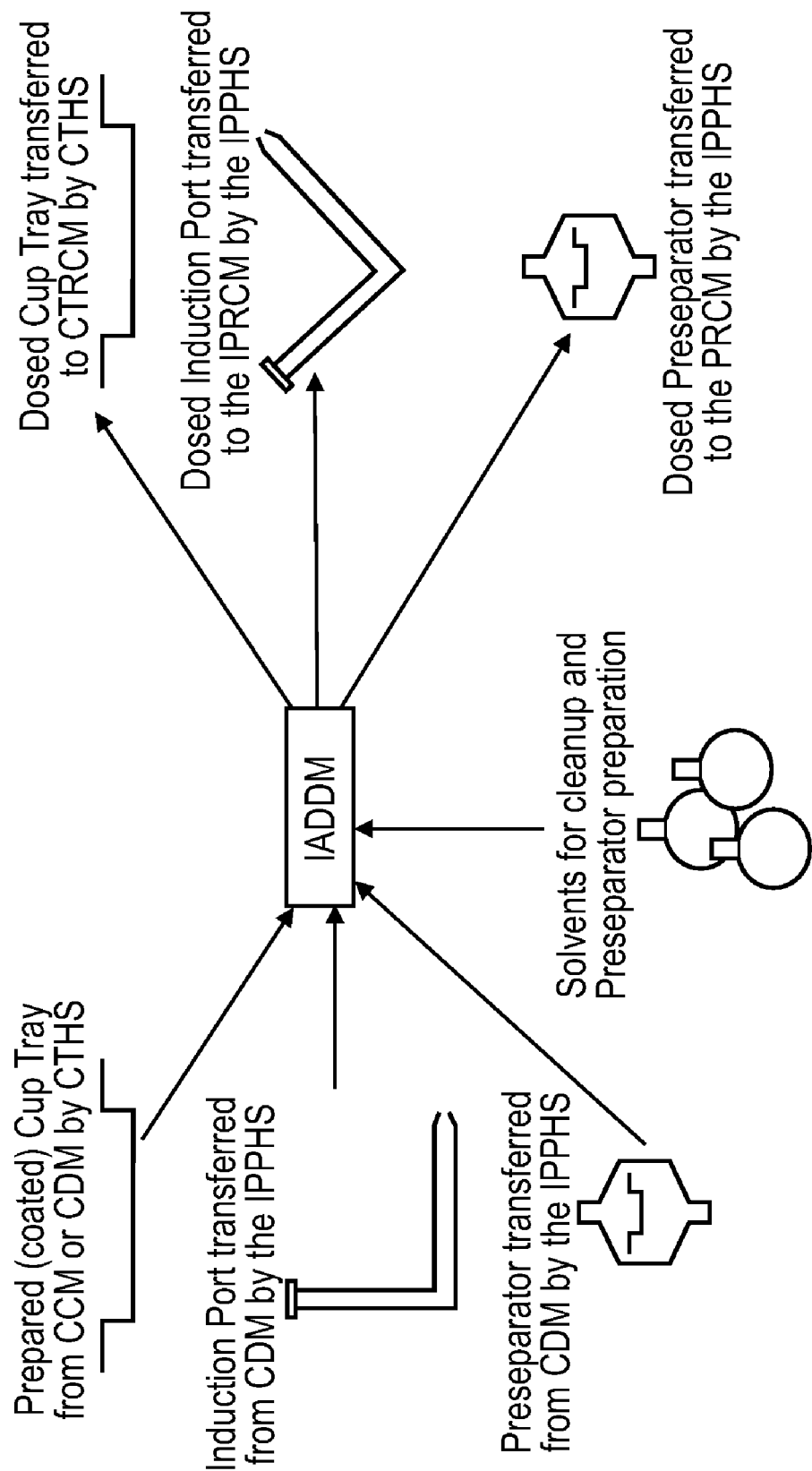
FIGS. 2a-h illustrate an impactor assembly, dosing and disassembly module of the system, FIG. 2a being a highly schematic representation of the processes carried out by this module, FIG. 2b being a perspective illustration of a stand and related components, FIG. 2c being an elevation of the module, FIG. 2d being a perspective illustration of a transfer mechanism, FIG. 2e being a schematic representation of a flow channel used in the module, FIG. 2f being a perspective illustration of an impactor head wash unit, FIG. 2g being a further perspective illustration of the transfer mechanism, and FIG. 2h being a perspective illustration of a nozzle tray modified in accordance with the present invention.

The functions of the IADDM module 200 are represented schematically in FIG. 2a. It serves to assemble the impactor 10 after preparation of its component parts, to carry out the actual dosing of the impactor 10 from the inhaler device (a process also referred to herein as "impaction"), and to disassemble the component parts of the impactor 10 ready for recovery of pharmaceutical material from them.

Figure 2B:
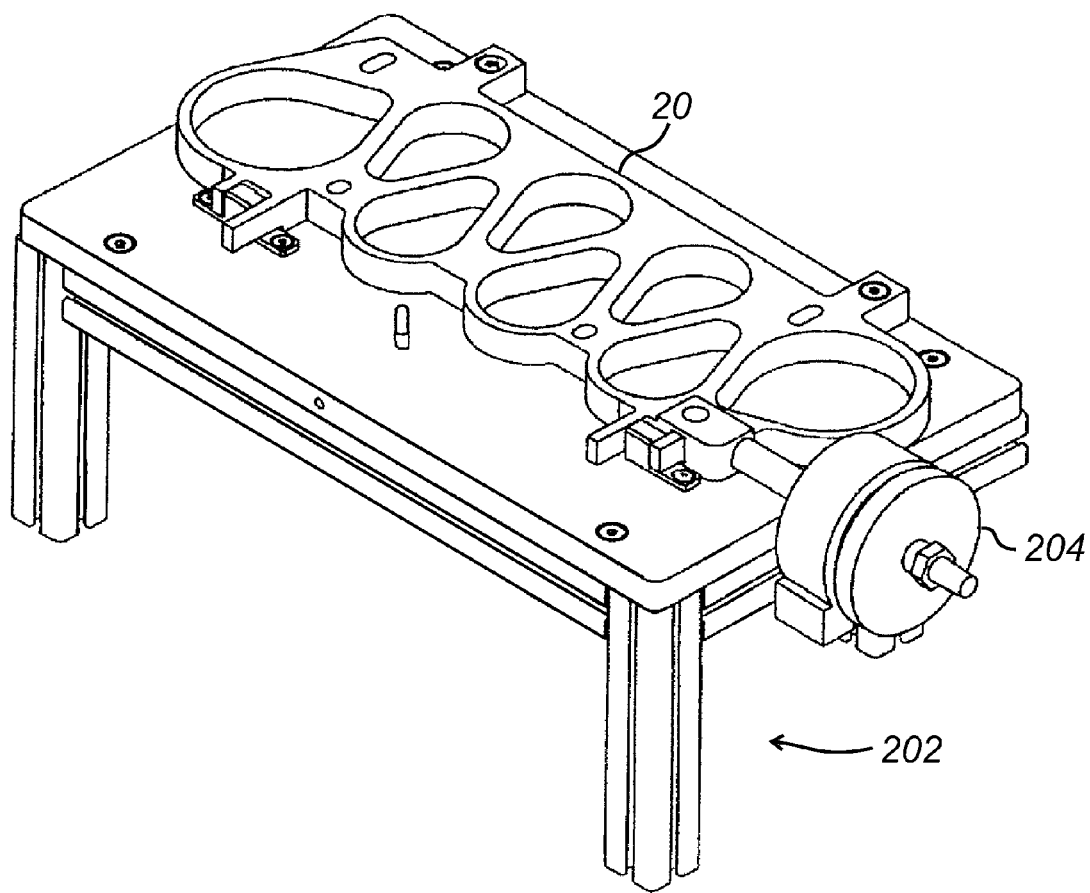

The base plate 20 of the impactor 10 is fixedly mounted upon a stand 202 (see FIG. 2b) and its exhaust is connected via an optional protective filter 204 to a vacuum flow channel 206 (see FIG. 2e) leading to a vacuum pump 208, to draw the aerosol through the impactor 10.

Figure 1A:
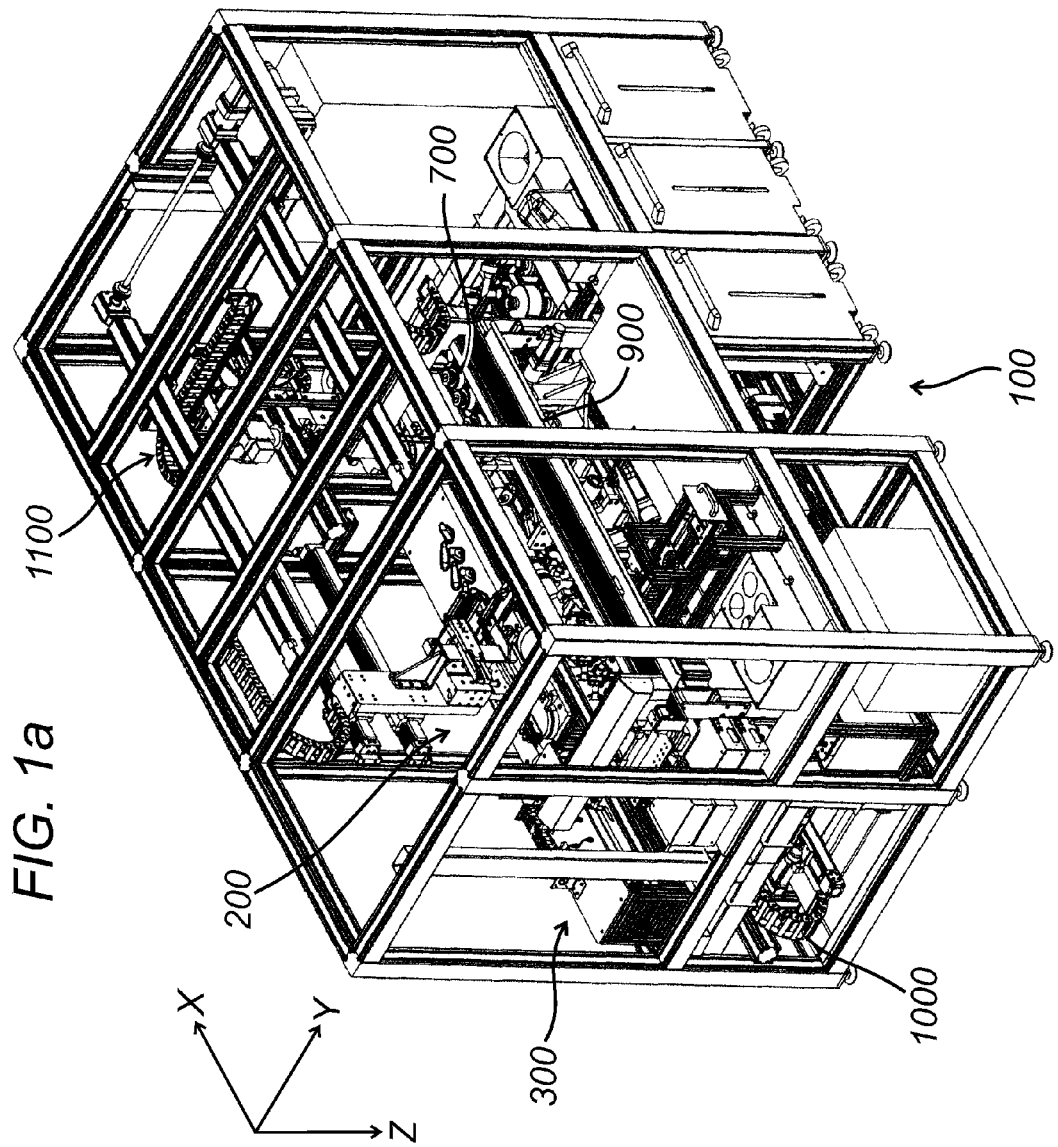

The impactor head 18 is mounted on an IADDM transfer mechanism 210 (see FIG. 2d in particular) comprising a traveler 212 mounted upon guide rails 214 extending in the X direction of the system (the X, Y and Z directions, or equivalently the side-to-side, fore-and-aft and up-and-down directions, are marked on FIG. 1a). Means are provided for moving the traveler 212 along the guide rails. Numerous suitable devices are known to those skilled in the art, but in the present embodiment the rails 214 form the cylinders of linear pneumatic actuators. The actuators move the traveler 212 between two end stops, defining its two operative positions. The details of the pneumatic actuators is not illustrated, since such devices are well known to those skilled in the art. The traveler 212 carries an impactor head actuator 216 (FIG. 2*c*) which carries the impactor head 18 and acts along the Z direction to advance/withdraw the impactor head for assembly/disassembly of the impactor. The impactor head actuator 216 also serves, when the impactor 10 is assembled, to urge the impactor head 18 into sealing engagement with the base plate 20 with a controlled clamping force.

The clamping force has a potential bearing upon the performance of the impactor because the head 18 and base plate 20 are separated by shallow resilient sealing rings surrounding each of the cups 24, to provide each impaction stage with the necessary air tight seal. An inadequate clamping force might not create the necessary seal. An excessive clamping force would, by excessive deformation of the seals, change the relative positions of the impactor components, and so could change impactor performance. To control the clamping force, the impactor head actuator 216 is supplied with air at controlled pressure by an electro pneumatic regulator (which is not depicted, but is of a type known to those skilled in the art). Note also that the impactor head 18 has a resilient mounting, to equalise the clamping pressure across its length and width despite any minor misalignment. Specifically, the clamping force is transmitted to the impactor head 18 through compression springs 218. A transducer (which is not clearly seen in the drawings, although its movable tip is just visible at 219) is a low voltage ("LVDT"—low voltage displacement transducer) device. Its sensor tip 219 is depressed by a bracket 221 (FIG. 2*g*) carried upon the impactor head 18, in order to measure the position of the impactor head 18 when it is clamped in place, so that mis-positioning of the head, due to wear of its seals, for example, or to misalignment of the head 18 and base plate 20, triggers an error handling procedure.

Figure 2C:
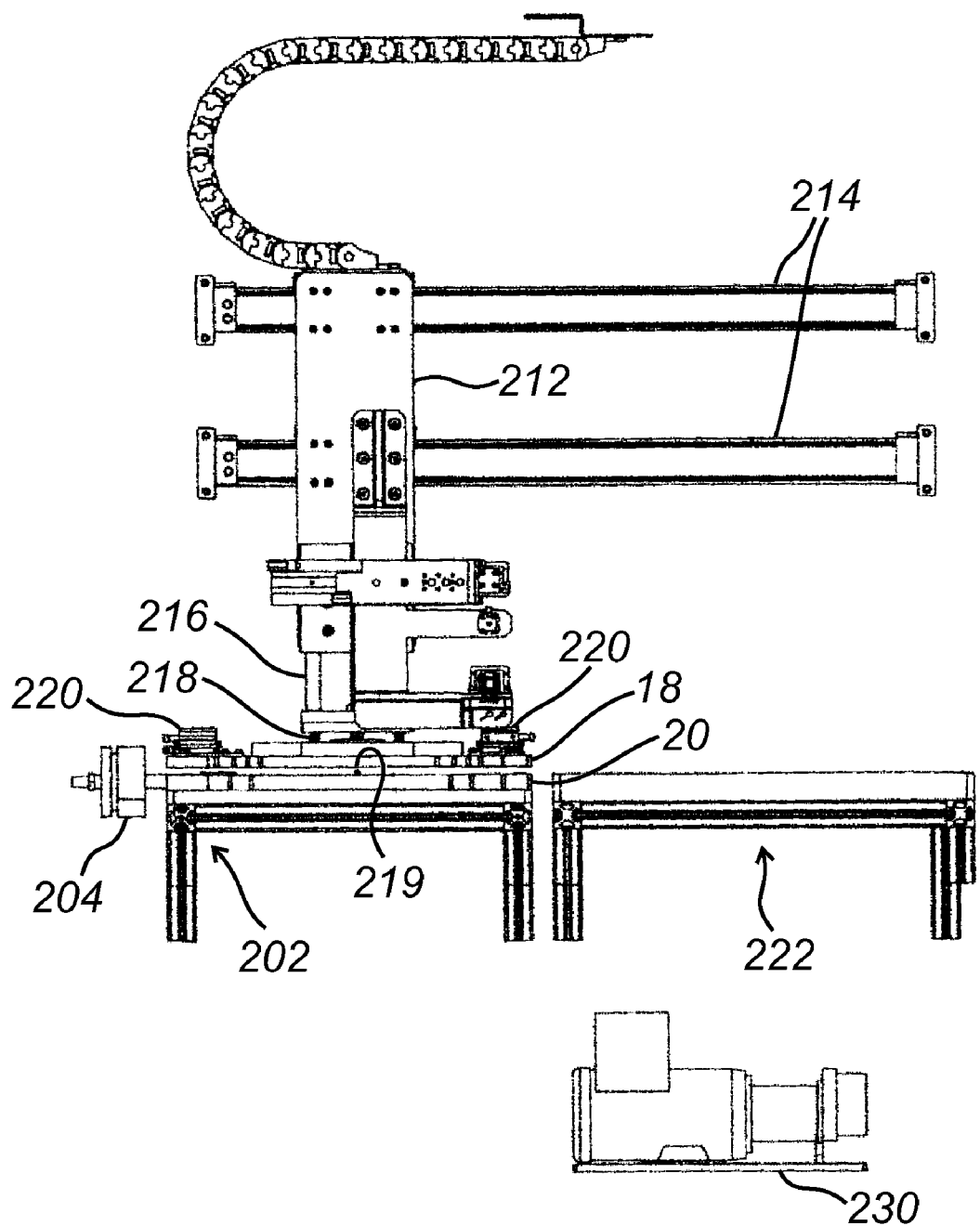
Figure 2D:
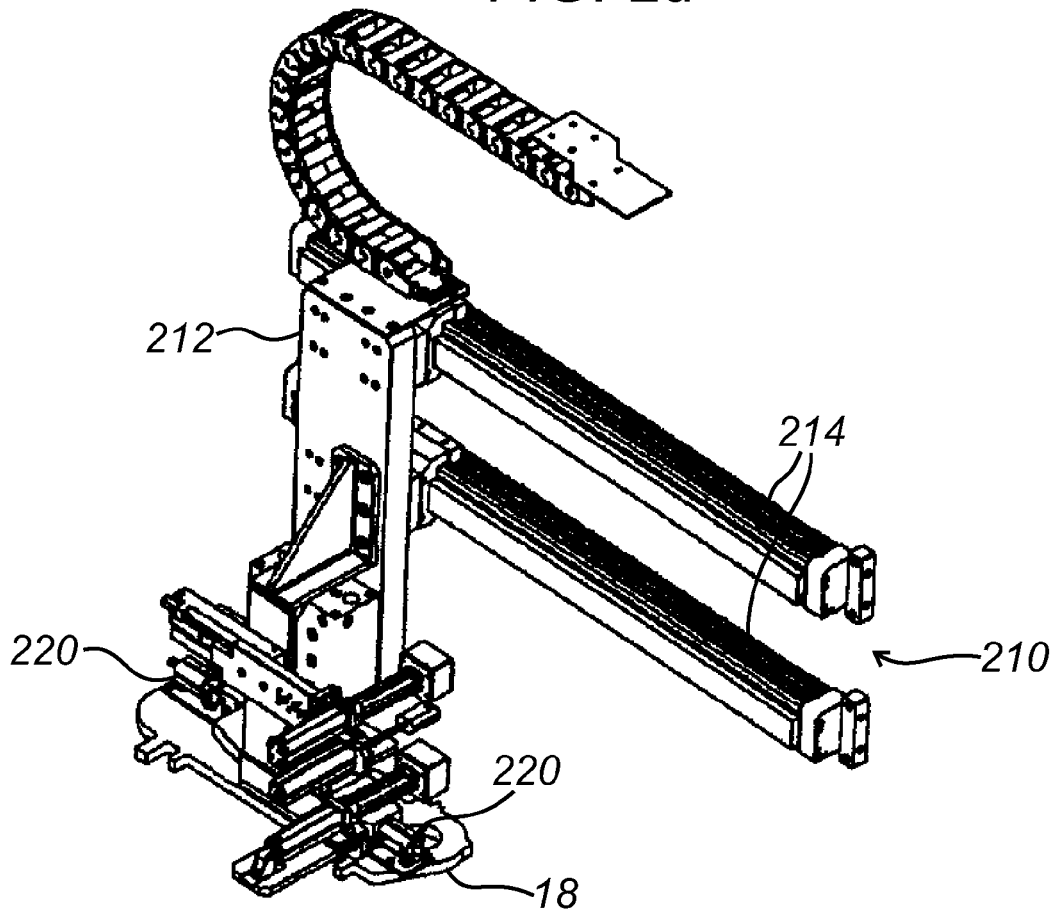
Figure 2E:
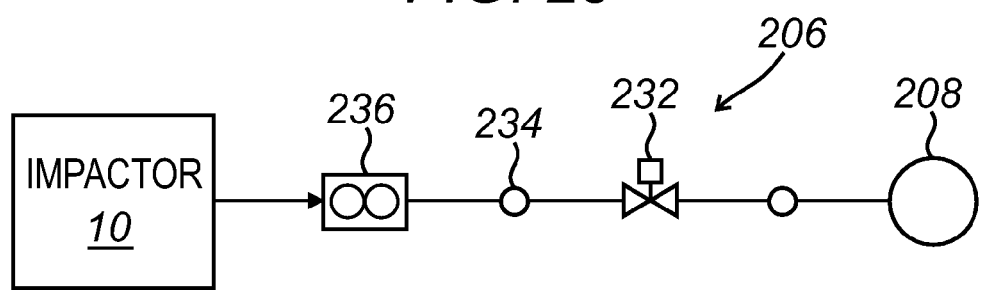
Figure 2F:
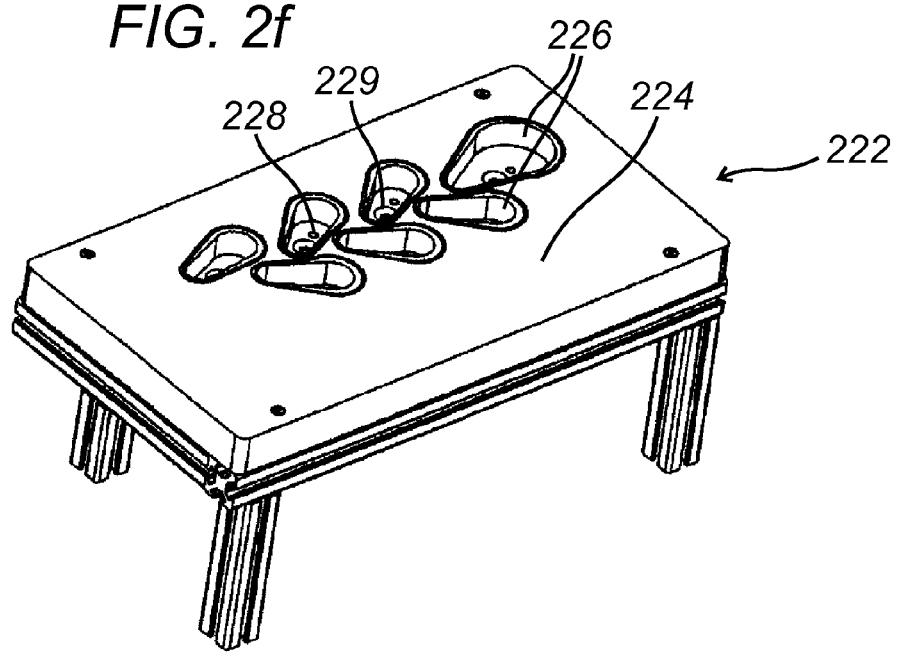
Figure 2G:
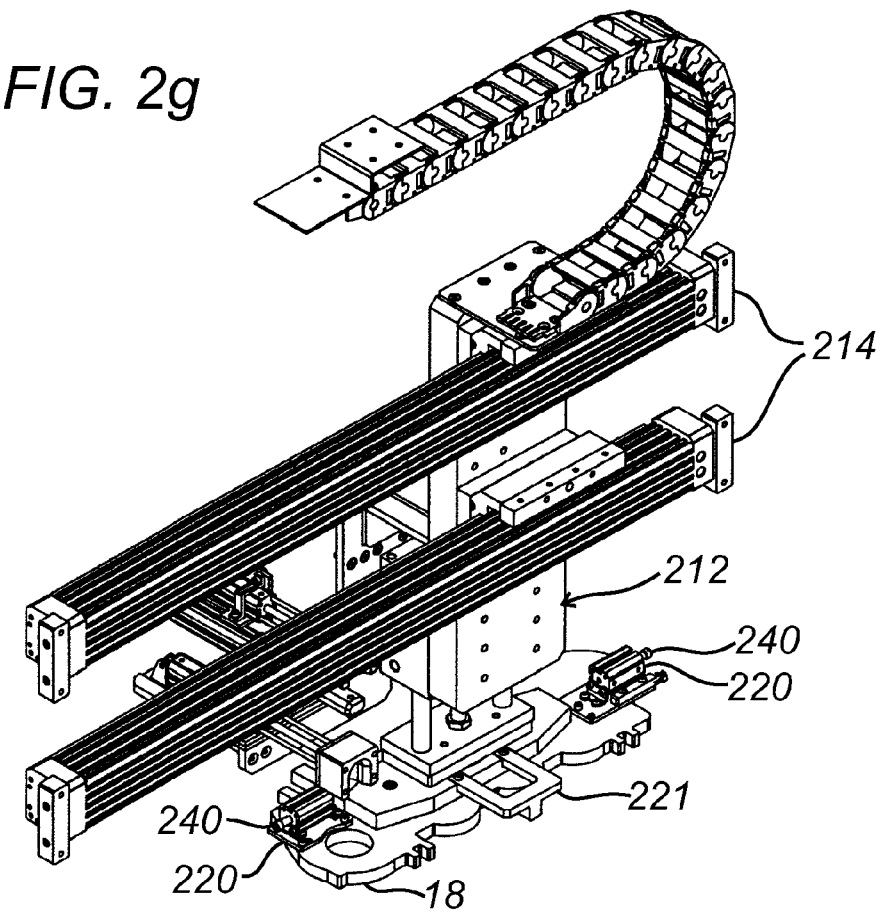
Figure 2H:
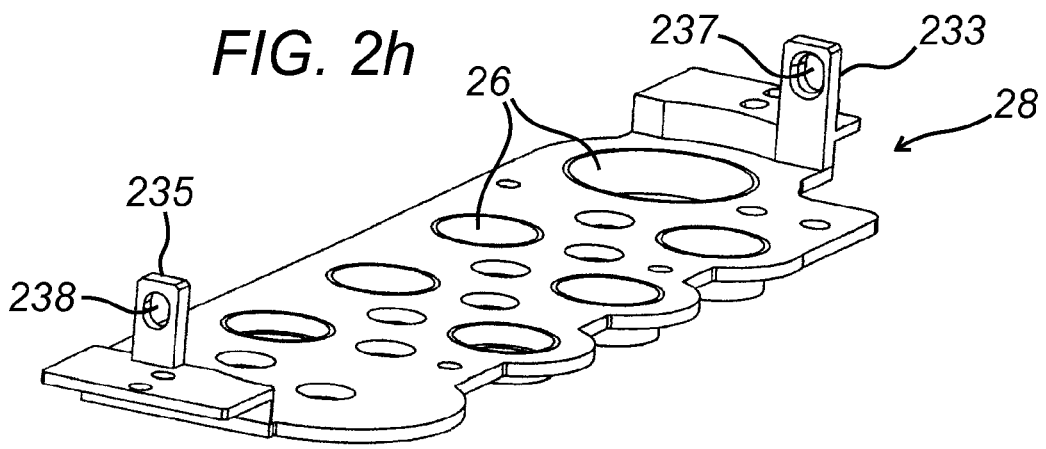

For recovery and clean up, the nozzle tray 28 is to be separated from the impactor head 18. To this end, it is releasably retainable beneath the impactor head 18 by means of an opposed pair of pneumatic nozzle tray attachment clamps 220 (see e.g. FIG. 2*g*) disposed at either end of the impactor head 18. FIG. 2*h* shows a nozzle tray 28 which has been modified (as compared with the known version seen in FIG. 12) in accordance with the present invention. It has a pair of upstanding carrying brackets 233, 235 at its opposite extremities, and these are arranged on the line about which the nozzle tray 28 balances, so that when suspended through openings 237, 238 the nozzle tray 28 is approximately horizontal—i.e. lying approximately in the X-Y plane of the system. As shown in FIG. 2*g*, the attachment clamps 220 each have a respective movable bolt 240 insertable through a respective opening 236, 238 to engage the nozzle tray 28, and raising the head 18 causes the nozzle tray 28 to be suspended from the bolts. Note that the openings 236, 238 are oversize so that when the impactor is assembled they do not carry any of the clamping force.

The amount of pharmaceutical material collected on and in the impactor head 18 is small, and this need not be collected for analysis. Clean up of this component is not required after every use. However experience has shown that periodic clean up is needed, and to this end the IADDM module includes an impactor head clean up unit 222 (FIGS. 2*c* and 2*f*). When necessary the impactor head 18 is placed on this unit by means of the IADDM transfer mechanism 210, the nozzle tray 28 being released from it and left on the base plate 20. The impactor head clean up unit 222 has a contact plate 224 provided with recesses 226 arranged to align with the nozzle and outlet openings 26, 30 of the impactor head 18. Through spray nozzles 228 formed in the recesses, cleaning fluid can be jetted onto the interior surfaces of the impactor head. Drainage openings 229 are used to exhaust the liquid after use.

Prior to dosing, to test the seal integrity between the impactor components, a leak test may be carried out by the IADDM module. In this process a bung is presented to the impactor inlet formed by the induction port 14. Vacuum pump 208 (FIG. 2*e*) is run to create low pressure in the impactor 10. Proportional solenoid valve 232 is opened slightly to admit air, until a chosen (sub-atmospheric) pressure is detected by an absolute pressure transducer 234, at which point the valve 232 is closed. Pressure rise at transducer 234 is then monitored over a chosen period, excessive pressure rise indicative of poor seal integrity triggering an error handling routine.

Also prior to dosing a flow adjustment sequence may be carried out, to determine what valve aperture is required to achieve the specified flow rate through the inhalation device. This is done using a dummy device having the same flow resistance characteristics as the real device (without releasing pharmaceutical). While a partial vacuum is applied to the impactor 10 by the vacuum pump 208, the opening of the proportional solenoid valve 232 is adjusted based upon flow rate measured by flow meter 236, in a closed loop, until the desired flow rate is achieved.

Dosing involves introduction of an inhaler device to the induction port 14 (the means used for this, which must be specific to the device, are not shown herein and do not themselves form part of the present invention, but suitable robotic devices are known to those skilled in this art) and application of a partial vacuum for a chosen period. A single dose, or multiple doses, may be fired in to the impactor 10 in this way in each cycle.

The impactor is then disassembled for recovery and clean up.

Cup Coating Module (CCM) 300

Figure 3A:
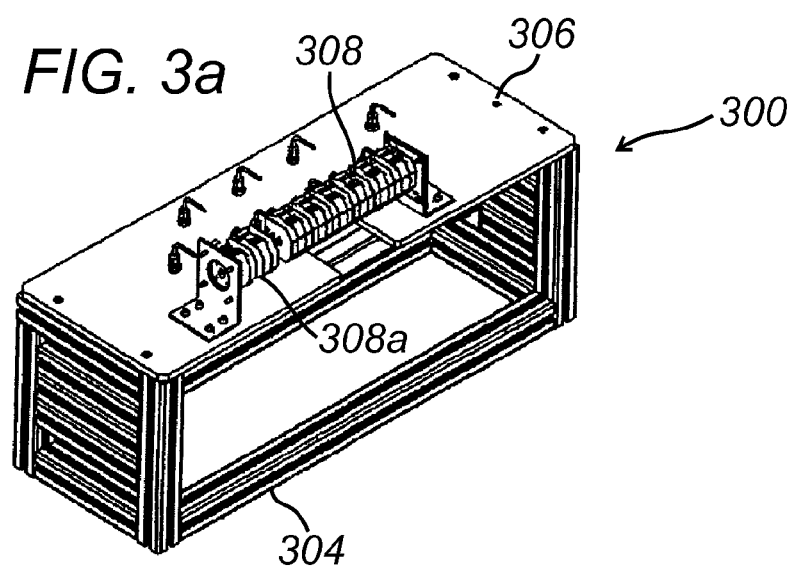
FIGS. 3a-b illustrate a cup coating module used in the system, FIG. 3a being a perspective illustration from the front and to one side of the module, and FIG. 3b being a side elevation.
Figure 3B:
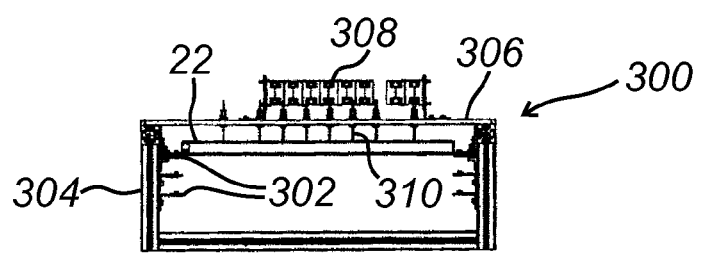

The cups 24 of the impactor 10 may in some applications require pre-coating with a substance which promotes adhesion of the particles in the aerosol to the cups 24. The substance may be silicone. This may be applied by applying a liquid comprising silicone oil and hexane to the cups 24. Being volatile, the hexane evaporates away quickly after application to leave behind an acceptably uniform silicone coating. After clean up the cup tray 22 is delivered to the cup coating module 300 (FIG. 3*b*) by means of the tray handling system (THS) 1000, being positioned on the cup coating module 3000 on ledges 302 of a support structure 304 beneath a carrier plate 306. There are three of sets of ledges, to allow three cup trays 22 to be stored, and when necessary the trays are re-arranged using the CTHS 1000 to place the tray to be coated on the top set of ledges 302. Upon the carrier plate 306 are multiple peristaltic pumps 308 to supply respective, controlled quantities of coating fluid through respective outlets 310 onto the cups beneath. The first and last impactor cups are larger than the others and their associated pumps 308*a* correspondingly have a larger working volume than the remaining pumps, to deliver a larger quantity of fluid.

Cup Tray Recovery and Collection Module (CTRCM) 400

After dosing, the cup tray 22, carrying pharmaceutical material to be recovered, is transferred by the CTHS 1000 from the IADDM module 200 (FIGS. 2*a-h*) to the cup tray recovery and collection module 400 (FIGS. 4*a-d*), which serves to deliver a controlled quantity of solvent to each cup 24, then to agitate the cup tray 22 to promote dissolution of the collected pharmaceutical in the solvent, then to facilitate collection of a sample of the resulting solution from the cups by the fluid handling robot (FHR) 900, and finally to carry out clean up and first stage drying of the cup tray 22.

A bottom plate 402 of the CTRCM module 400 is recessed to receive the cup tray 22 and is disposed beneath a top plate 404, so that the cup tray 22 can be sandwiched between the two. The bottom plate 402 is mounted for movement along the Z direction upon a pneumatic actuator 406. The actuator 406 is in turn mounted to the top plate 404 through brackets 408, and the resulting assembly is suspended from pivot bars 410 projecting from opposite ends of the top plate 404. Note that on its underside the top plate 404 has resilient seals 412 whose shapes and positions correspond to those of the cups 24. In use, the bottom plate 402 is first moved away from the top plate using actuator 406, to allow the cup tray 22 to be inserted by the CTHS 1000. The bottom plate 402 is then urged against the cup tray and urges the cup tray 22 against the top plate 404, so that each cup 24 forms a separate, sealed recovery chamber along with the adjacent top plate 404.

A support framework 414 carries bearings 416 which receive the pivot bars 410 and so mount the assembly, allowing it to rotate about an axis which is generally horizontal (i.e. generally in the X-Y plane). Within a guard 418 is a drive mechanism coupled to a servo motor 420 for applying a rocking motion to the assembly. That is, the assembly is swung back and forth to either side of its upright position, in the manner of a baby's cradle. This provides the agitation necessary to promote dissolution of the pharmaceutical in the solvent.

Figure 4A:
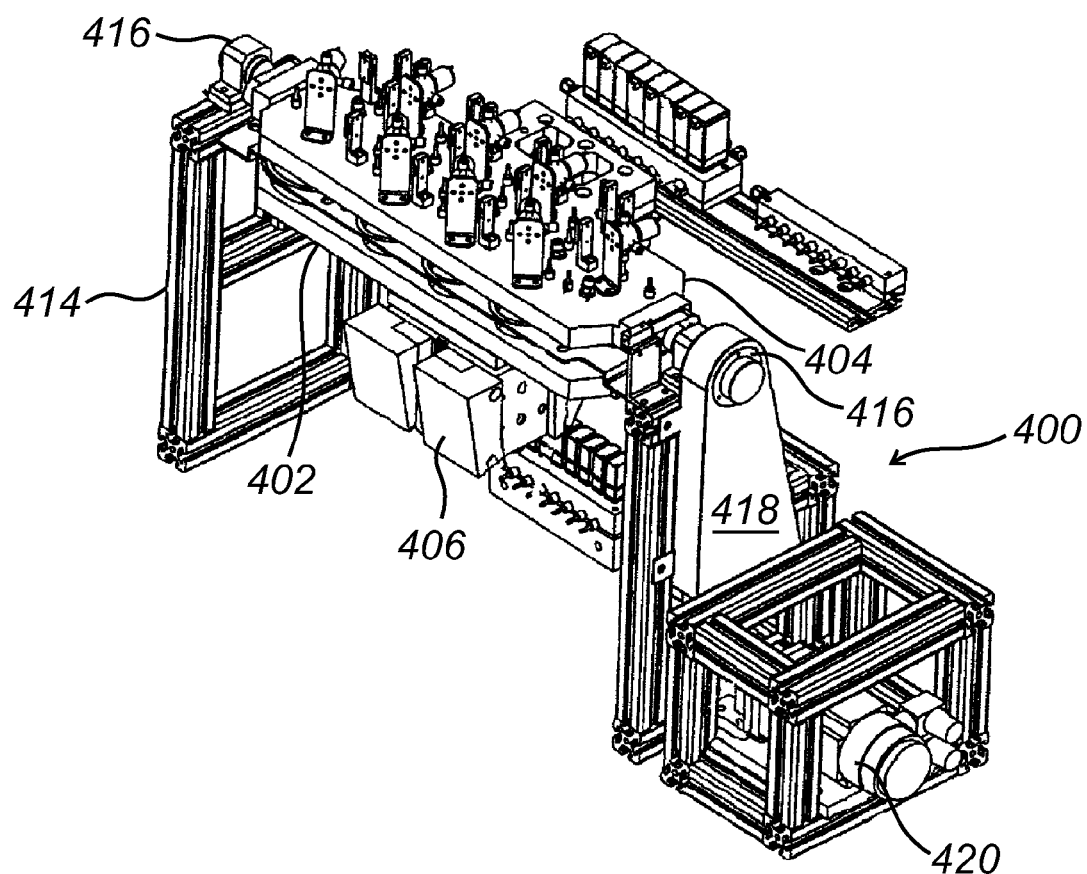
FIGS. 4a-d illustrate a cup tray recovery and collection module of the system, FIG. 4a being a perspective illustration of the module from the front and to one side, FIG. 4b being a scrap view of a subassembly of the module, FIG. 4c being a perspective illustration of it from the rear and to one side, and FIG. 4d being a schematic representation of fluid connections and related components of the module.
Figure 4B:
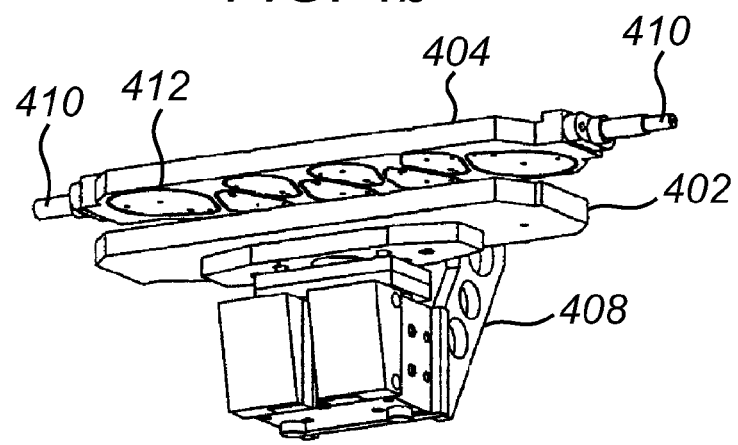
Figure 4C:
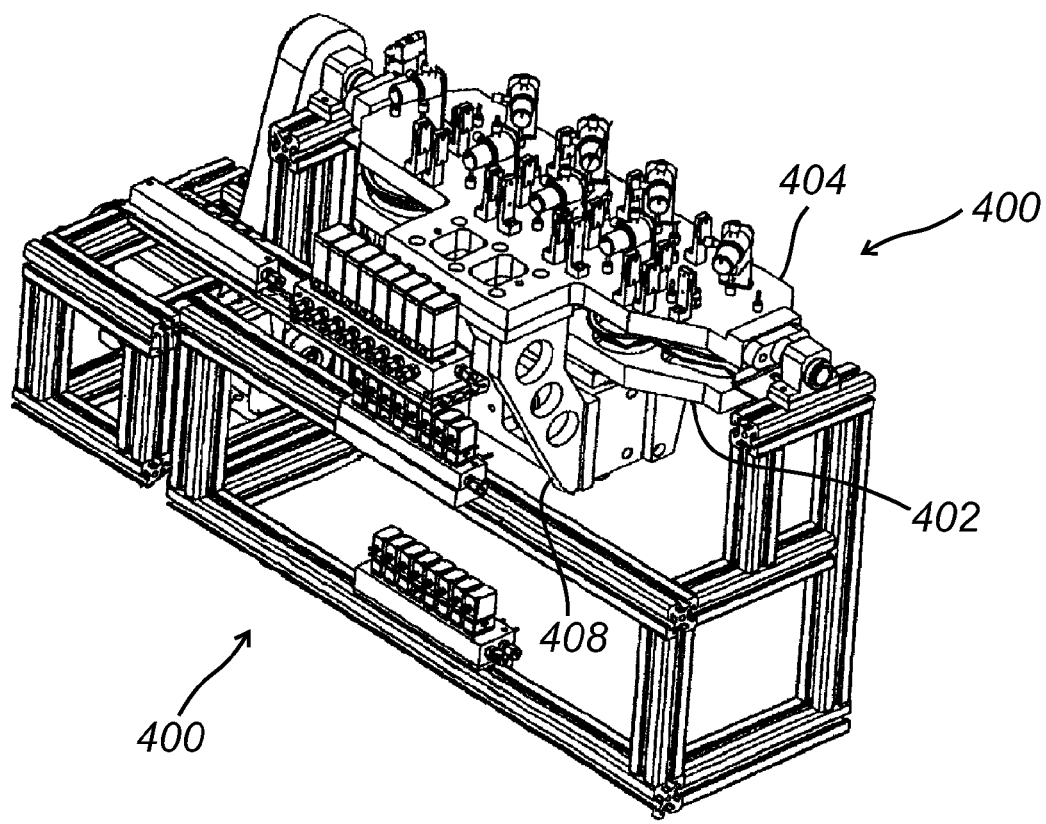
Figure 4D:
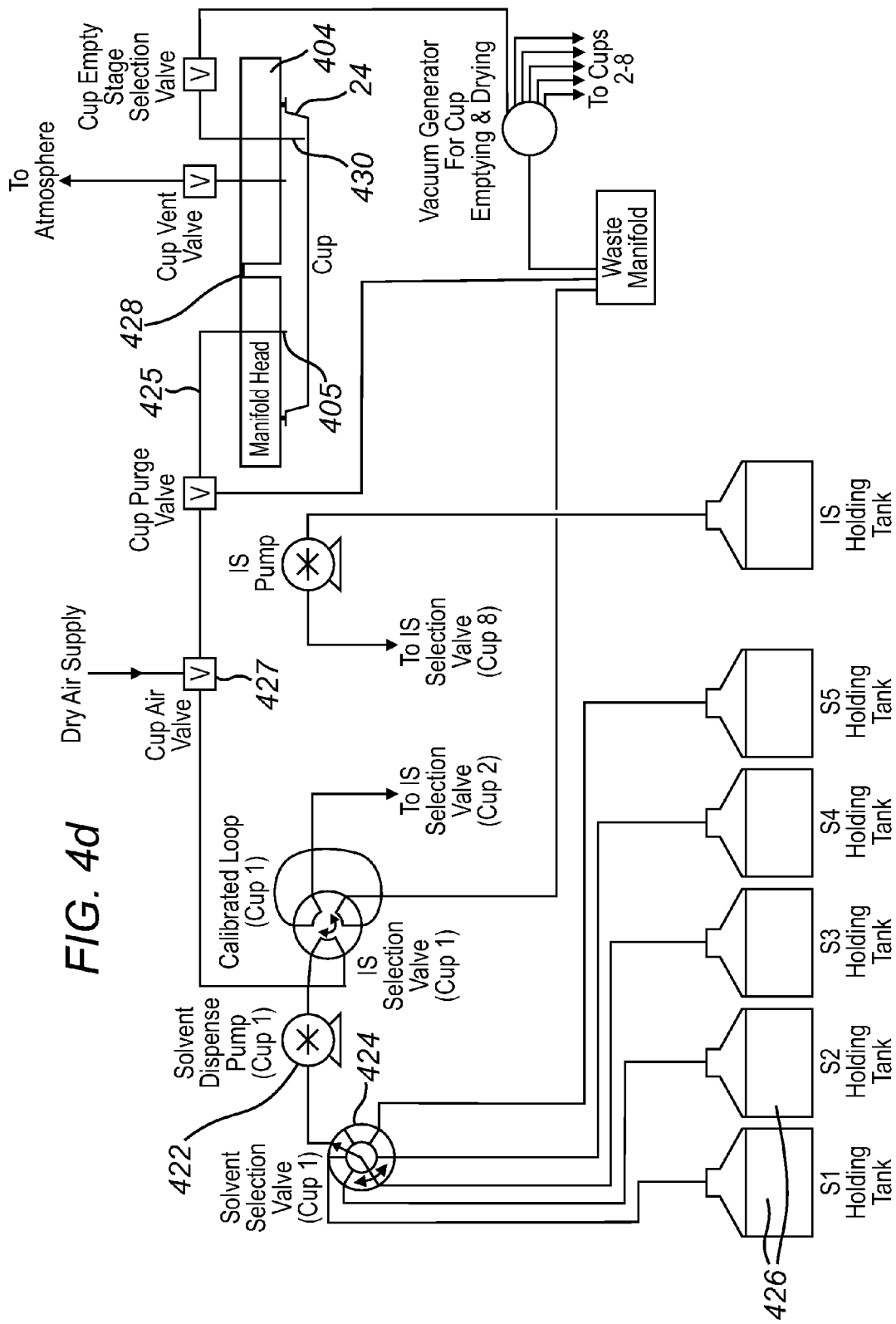

Each cup 24 has an associated fluid delivery and exhaust system, one of which is schematically represented in FIG. 4*d*. Solvent dispense pump 422 is a displacement type pump arranged and calibrated to draw a controlled quantity of solvent via a solvent selection valve 424 from any of a set of holding tanks 426. In the illustrated embodiment there are five of these, and any combination of the solvents can be used, under software control. Other modules which carry out solvent delivery are likewise able to draw any of the five available solvents, but to avoid repetition the fluid connections will not be illustrated and described for each. The solvent is delivered through a port 405 in the top plate 404 to the cup 24. At the end of each solvent dispense step, solvent remaining in the pipe 425 is ejected into the cup 24 by compressed air from means of an air valve 427. This ensures that the correct volume is dispensed and that no droplet forms on the nozzles. Agitation then takes place, as just described, to dissolve the pharmaceutical in the solvent.

The resulting solution in the cup will form one of the assays for analysis, and a quantity of it must be withdrawn and stored for this purpose. This is done using the fluid handling robot 900 (see FIG. 9), whose collection needle is inserted through a self sealing resilient septum in the top plate 404, this component being schematically represented at 428 in FIG. 4*d*. Note that the cup 24 is shallow and flat bottomed, so that withdrawal of fluid could in principle be problematic due to small fluid depth in it. Such problems are avoided by inclining the cup tray 22, using the drive mechanism, causing fluid to flow toward the low end of the cup to locally increase its depth. Note that each cup 24 has a narrow end and a wider end. To maximise fluid depth, the cups are to be inclined downwardly toward their narrow ends. Note also that the narrow cup ends alternate, with one cup having its narrow end toward the left or the impactor and its neighbours having their narrow ends toward the right. Hence the process involves inclining the impactor 10 first one way, to collect from cups 1, 3, 5 and 7, and then the other, to collect from cups 2, 4, 6 and 8. Although the septum 428 is schematically shown in the middle of the cup 24 in FIG. 4*d*, it is in fact positioned toward the cup's narrow end. The fluid handling robot's needle is inserted though each septum, 428 while the assembly is inclined, into the region where fluid depth is greatest.

After collection of all the required samples the cup tray 22 is to be emptied and cleaned. Emptying of each cup 24 is carried out through an exhaust 430, again arranged at the narrow end of the cup so that to minimise the liquid quantity left in the cup 24, the cup tray 22 is suitably inclined. Cleaning involves dispensing a quantity of cleaning solution to each cup via the solvent dispense pump 422 and solvent selection valve 424, then agitating as previously described, then once more emptying the cups. The clean cup tray 22 is then transferred to the cup coating module 300, for coating and storage, by the tray handling system 1000.

Induction Port Recovery and Collection Module (IPRCM) 500

Figure 11A:
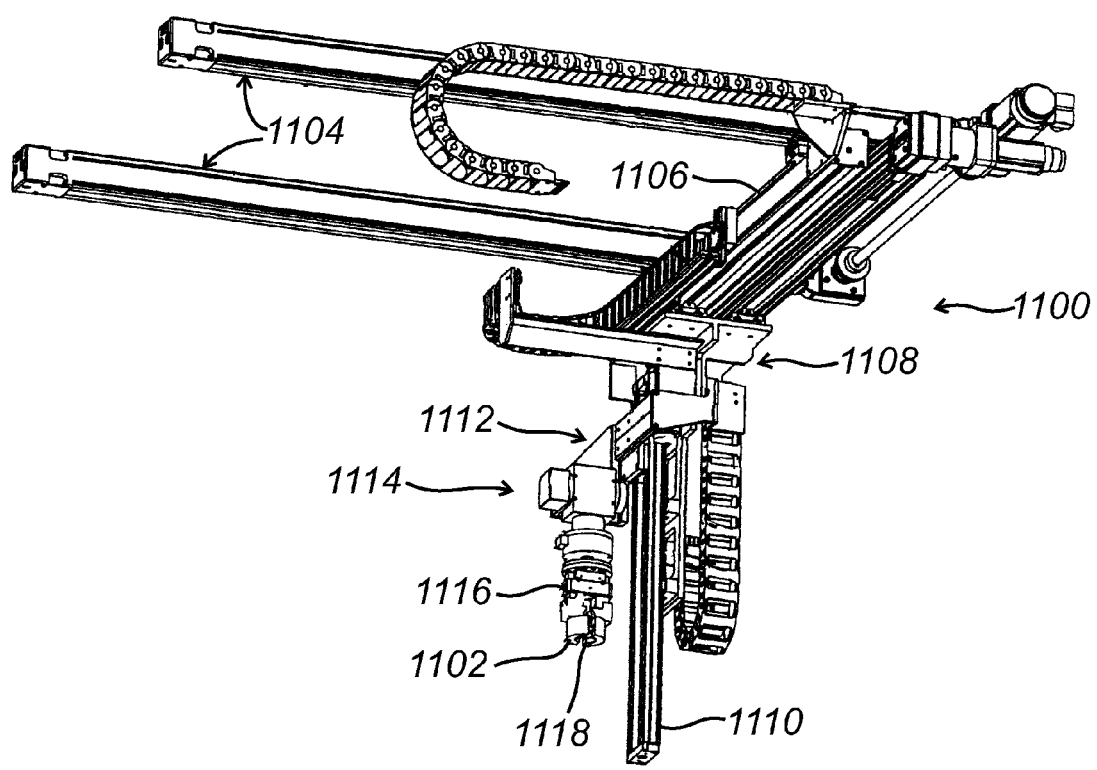
FIGS. 11a-c illustrate an induction port and preseparator handling system, FIG. 11a being a perspective illustration of the system from beneath, FIG. 11b being a side elevation of it and the cup tray handling system, and FIG. 11c being a perspective illustration of a gripper assembly.
Figure 11B:
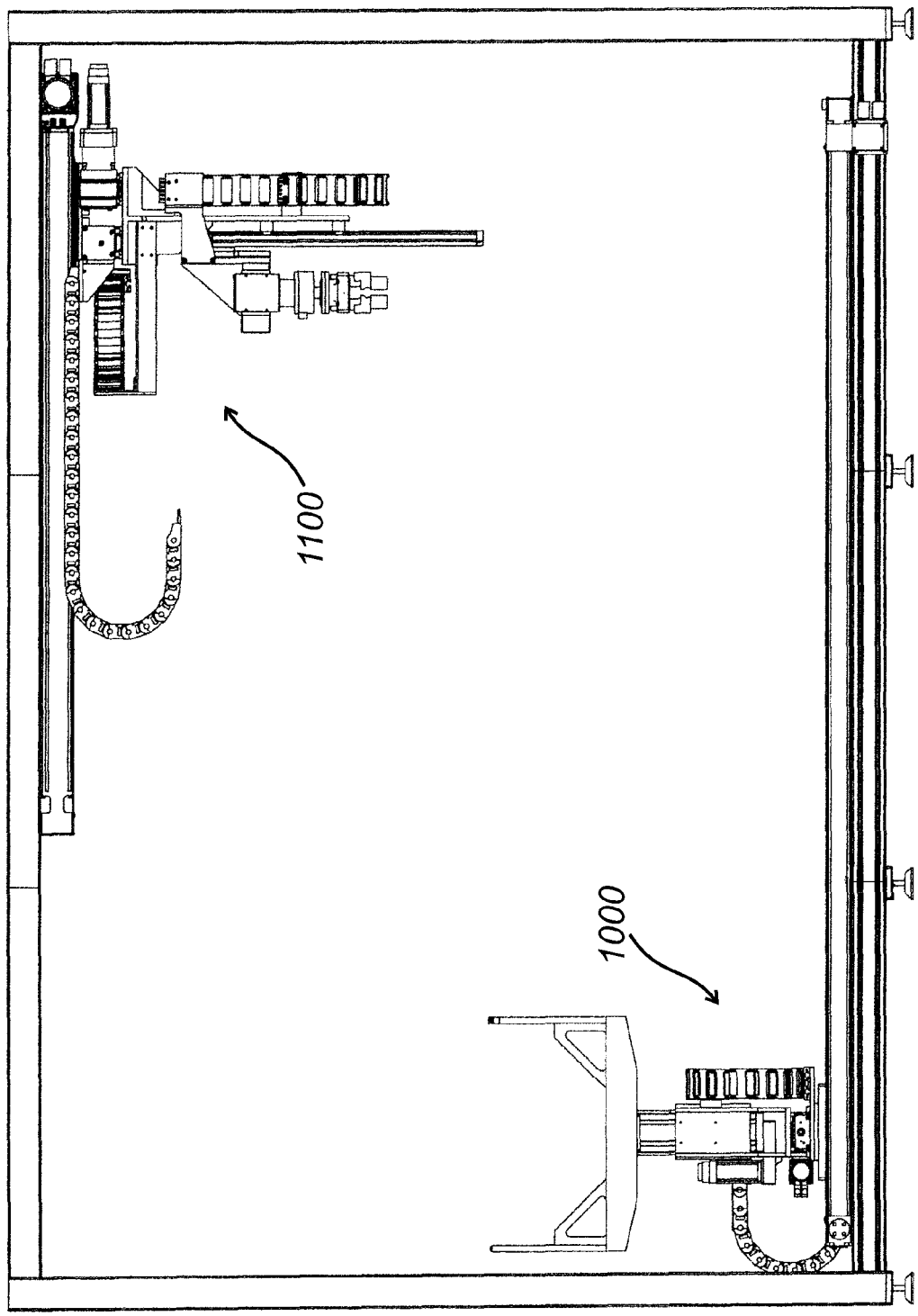
Figure 11C:
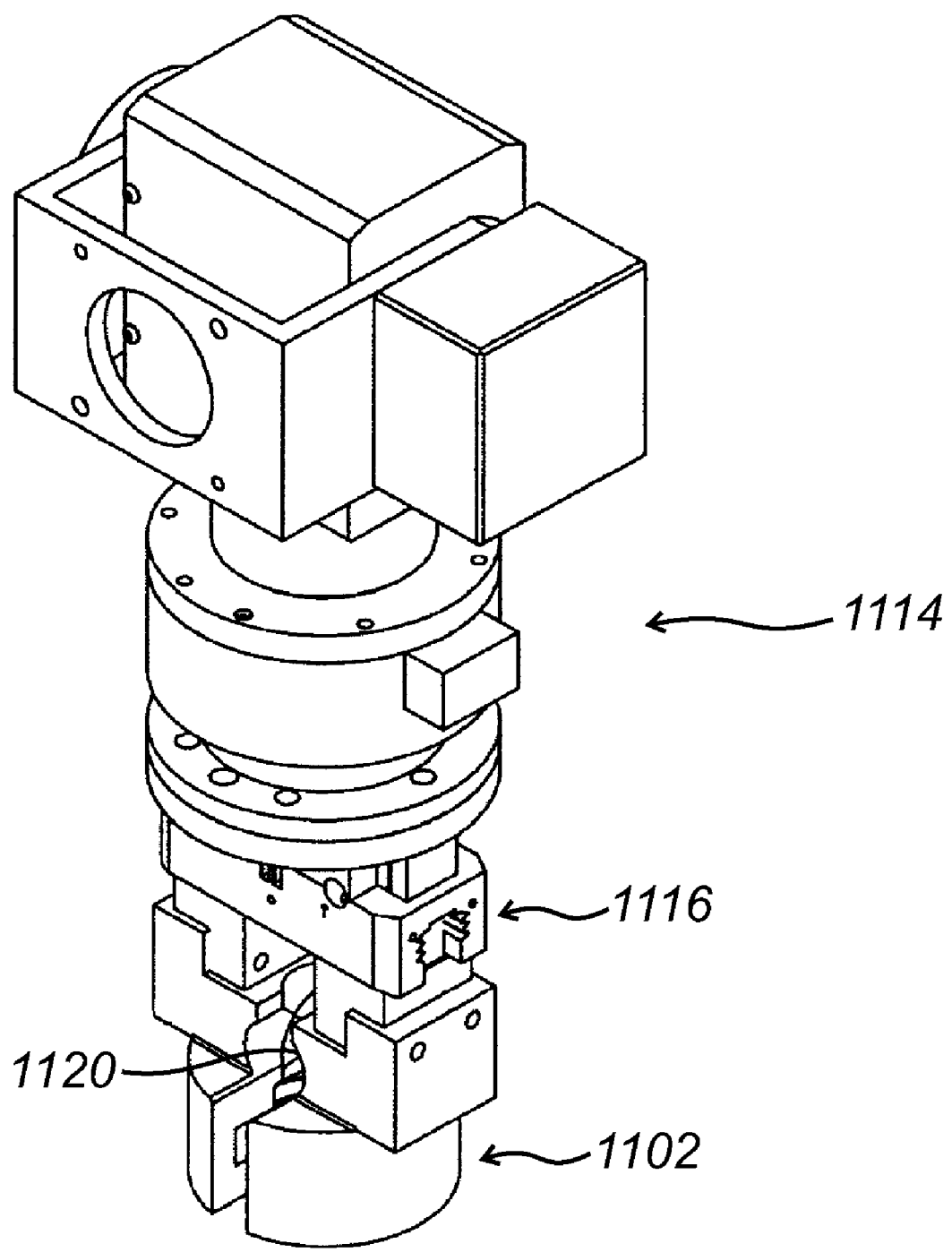

After dosing, the induction port 14, carrying pharmaceutical material to be recovered, is transferred from the IADDM module 200 to the induction port recovery and collection module (IPRCM) 500 (FIGS. 5*a-d*) by means of the induction port and preseparator handling system 1100 (FIGS. 11*a-c*). This serves to dispense a known quantity of solvent into the induction port 14, then to agitate it to promote dissolution of the collected pharmaceutical in the solvent, then to facilitate collection of samples of the resulting solution for analysis, and then to clean up the induction port ready for re-use.

Figure 5A:
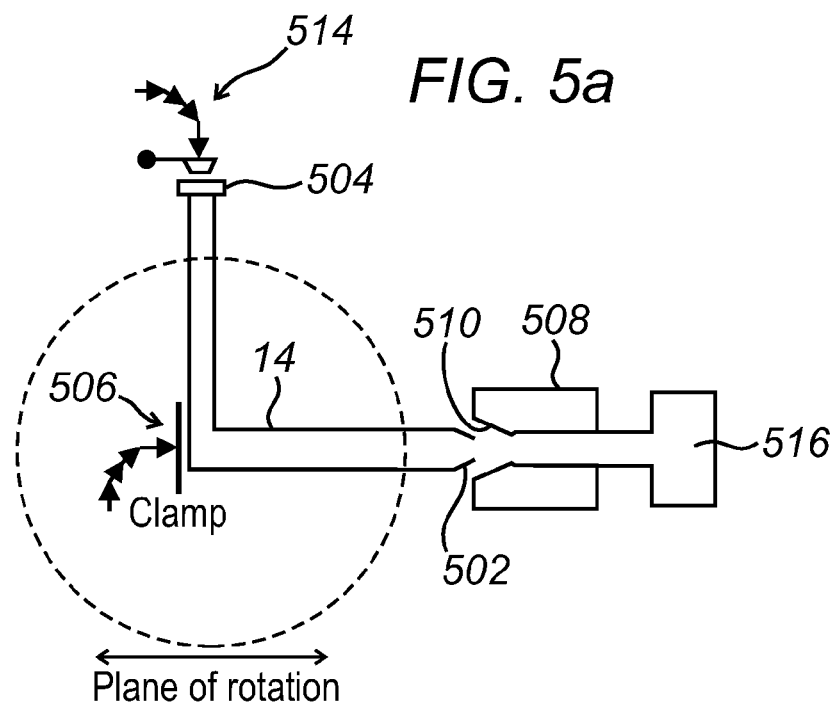
FIGS. 5a-d illustrate an induction port recovery and collection module of the system, FIG. 5a being a highly schematic representation of certain components of the module, FIG. 5b being a perspective illustration of it from the front and to one side, FIG. 5c being a scrap view of a seat used in the module, and FIG. 5d being a perspective illustration of the module from the rear and to one side.

FIG. 5*a* is a schematic representation of some parts of the IPRCM module 500. As mentioned above, the induction port 14 terminates, at its outlet end, in a tapered fitting. This is seen at 502. At its other end it has a mouthpiece 504, which may for example be formed of an elastomer, for seating against and sealing to the mouthpiece of the inhaler device. Both ends are to be closed, to form a sealed chamber within the induction port 14 for receiving solvent. This is done by means of an induction port clamping mechanism 506 which urges the tapered fitting 502 against a complementarily formed seat 508, having a tapered bore 510 to receive the tapered fitting 502, and a mouthpiece sealing mechanism 512. The induction module is then tumbled to agitate the mixture within. The word "tumble" is used herein to refer to rotational motion about a non-vertical axis. In the illustrated embodiment this axis is horizontal, and perpendicular to the plane of the paper in FIG. 5*a*. The tumbling motion could be about more than one axis. Note also that to increase the volume of solvent an extension chamber 516 communicates with the interior of the induction port 14 through the bore 510.

Figure 5B:
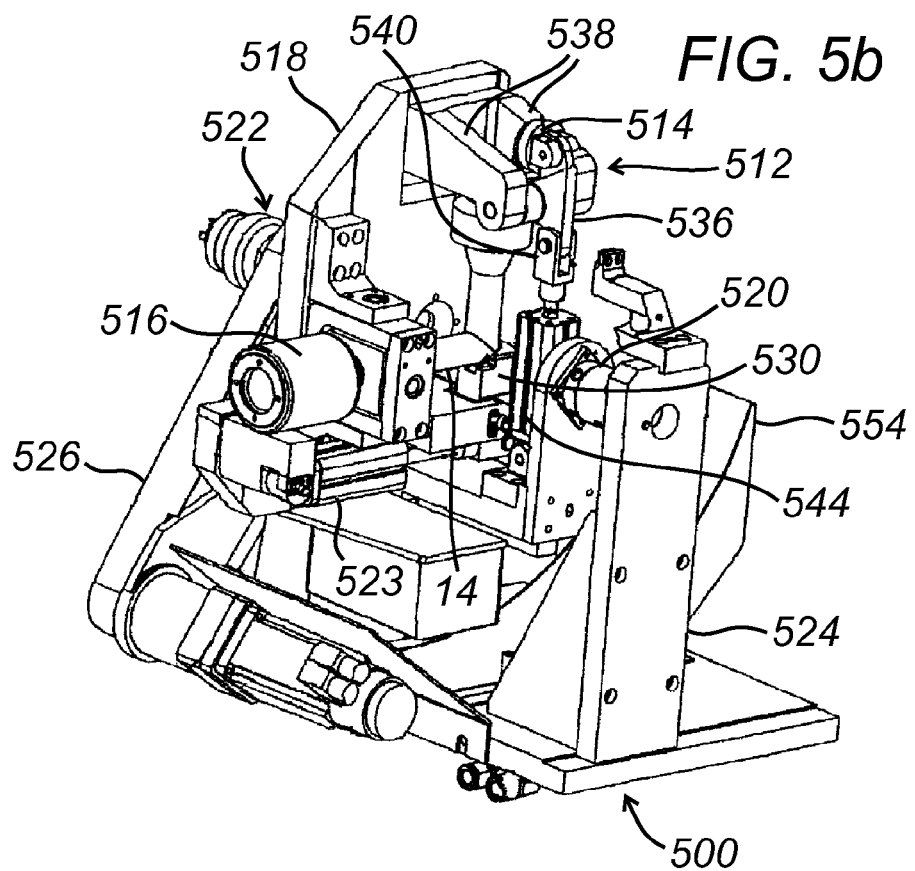
Figure 5C:
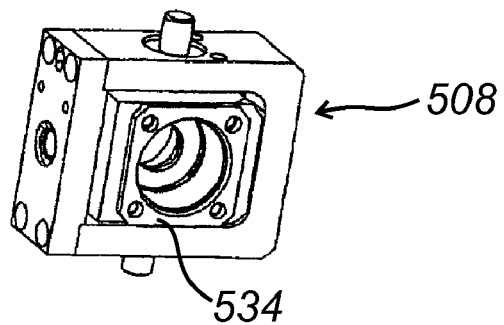
Figure 5D:
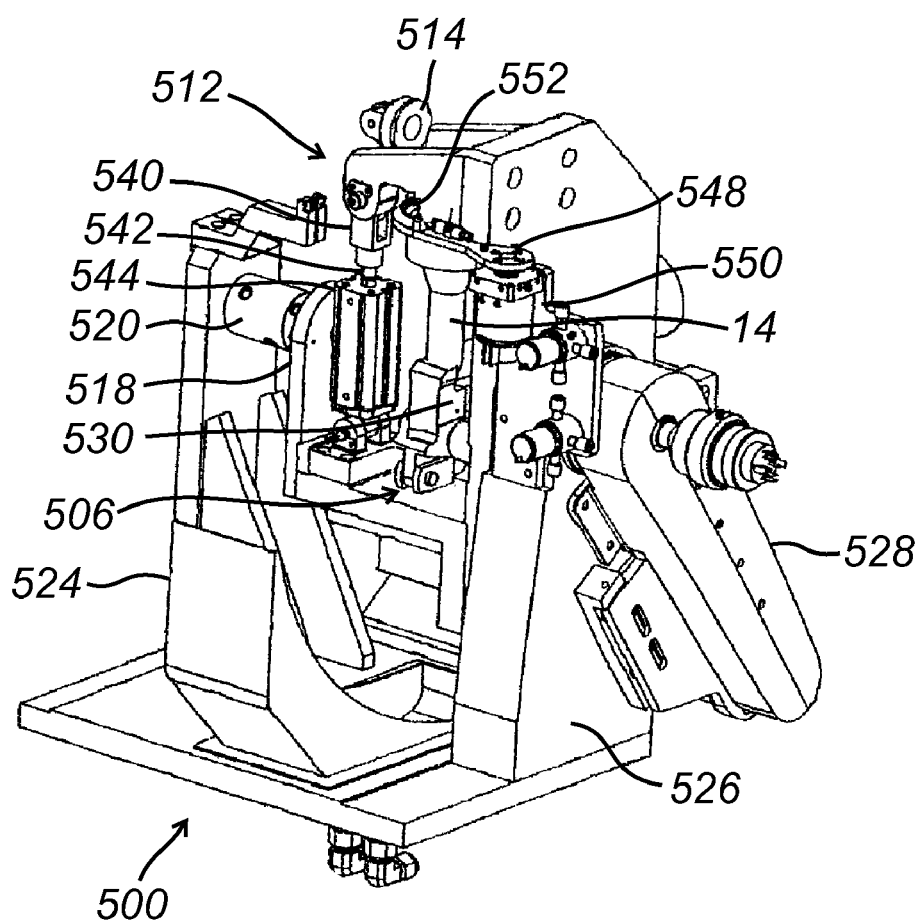

FIGS. 5*b-d* show the physical construction of the IPRCM 500. The mouthpiece sealing mechanism 512 and the induction port clamping mechanism 506 are carried upon an approximately "U" shaped rotor frame 518, forming an assembly which is rotatable about an axis defined by bearings 520, 522. The bearings are mounted upon fixed uprights 524, 526. A drive mechanism 528, including a servo motor and gearbox, is used to rotate the assembly about the said axis.

The elbow of the induction port 14 seats upon a shaped cradle 530 which is movable by means of a pneumatic induction port clamping actuator 523, to bring the cradle and the tapered fitting of the induction port 14 into engagement with the seat 508, seen in FIG. 5*c* to have a seal piece 534 shaped to receive and seal against the said fitting. The seat 508 communicates with an optional extension chamber 516, which is mounted upon the seat 534.

The mouthpiece sealing mechanism 512 comprises an arm 536 pivotally mounted between a pair of brackets 538 projecting from the rotor frame 518. On one side of its pivotal axis, the arm 536 has a pivotal coupling 540 to the piston rod 542 of an induction port sealing actuator 544. On the other side of its pivotal axis, the arm 536 carries a seal 514. The actuator 544 is thus able to move the seal 514 between a raised position (shown in the drawings) in which it is disengaged from the induction port mouthpiece 504, and a sealing position in which it closes the mouthpiece.

Delivery of solvent to the interior of the induction port 14 is made through a dispense arm 548 (FIG. 5d) mounted upon a rotary actuator 550. The rotary actuator 550 is mounted upon upright 526 and so does not rotate along with the induction port 14 during agitation, thus avoiding the need to form a fluid link to a rotating part. Instead, the dispense arm 548 is movable by means of the rotary actuator 550 between an operative position (seen in FIG. 5) in which it is positioned to dispense solvent via a conduit 552 into the open mouthpiece of the induction port 14, and a safe position in which it is withdrawn from the vicinity of the induction port and so does not foul the assembly carrying the induction port 14 during its rotation. Exhaustion of liquid is achieved by rotating the induction port 14 to pour its contents into a waste chute 554.

In operation, the induction port 14 is released from the impactor 10 by means of the induction port and preseparator handling system 1100 (FIGS. 11a-c), using a twist and pull action to release the tapered fitting 502, and is transferred by the same system to the IPRCM 500 where it is seated upon the cradle 530 and retained in position by the induction port clamping mechanism 506. Note that during its transfer, the induction port 14 is held with its elbow lowermost—i.e. it is arranged in a "V", with its open ends uppermost, to avoid spillage of collected pharmaceutical material. A controlled dose of solvent is introduced to the induction port, which is then rotated to agitate. A sample is collected using the fluid handling robot 900 (FIG. 9) through the mouthpiece 504, and the remaining solution is then poured into a waste chute 554 (FIG. 5b). Clean up is carried out by solvent addition and agitation.

Preseparator Recovery and Collection Module (PRCM) 600

After dosing, the preseparator 16, carrying pharmaceutical material to be recovered, is transferred from the IADDM 200 to the preseparator recovery and collection module (PRCM) 600 (FIGS. 6a-d) by the IPPHS 1100 (FIGS. 11a-c). The PRCM 600 serves to deliver a controlled quantity of solvent to the interior of the preseparator 16, then to agitate it to promote dissolution of the collected pharmaceutical in the solvent, then to facilitate collection of samples of the resulting solution for analysis, and to clean up the preseparator ready for re-use.

The preseparator 16 seats in a mounting cup 602. A generally "U" shaped support frame 604 carries the mounting cup 602 and is itself mounted for rotation about a generally horizontal axis between a pair of uprights 606. A single electric servo motor 608 provides two-axis motion of the mounting cup 602 and the preseparator 16, for agitation. Drive from the motor 608 is applied directly to the support frame 604 to turn it about its horizontal axis. Drive from the motor 608 is also transmitted, through a gear train, to the mounting cup 602, to spin the mounting cup about its own axis. The gear train comprises a first gear 612 which is fixed and lies upon the axis of rotation of the support frame 604 to engage with a second gear 614 mounted upon the support frame itself. Rotation of the second gear 614 is transmitted through further gearing carried on the support frame 604, comprising a third gear 616 meshing with the second gear 614 and coupled through a shaft to a bevel cog 618 which meshes at right angles with a bevel gear 620 coupled to the base of the mounting cup 602.

A spring loaded clamping yolk 621 is used to keep the preseparator 16 in position. It is pivotally mounted upon a clamp shaft 624, running between a pair of mounting stubs 626, and is urged toward its closed position (shown) by a torsion spring 628. The yolk 621 has a pair of fingers 630 carrying a clamp insert 632 which, in the closed configuration, abuts the upper periphery of the preseparator 16 to locate it. Release of the clamp is only possible while the support frame 604 is upright, as shown, and is achieved by means of a catch 634 having an undercut recess shaped to receive and engage an opening bar 636 at the rear of the clamping yolk 622. By pulling downwardly on this bar, the catch raises the yolk's fingers 630 and its insert 632, against the spring biasing, to release the preseparator 16. The force required for this is provided by an upright pneumatic release actuator 638 upon which the catch 634 is mounted. During agitation, the catch 634 is disengaged and both the catch 634 and the release actuator 638 are moved to a safe position, away from the path of the rotating assembly, using a pneumatic withdrawal actuator 640 which is mounted in a base plate 642 of the module 600.

Figure 6A:
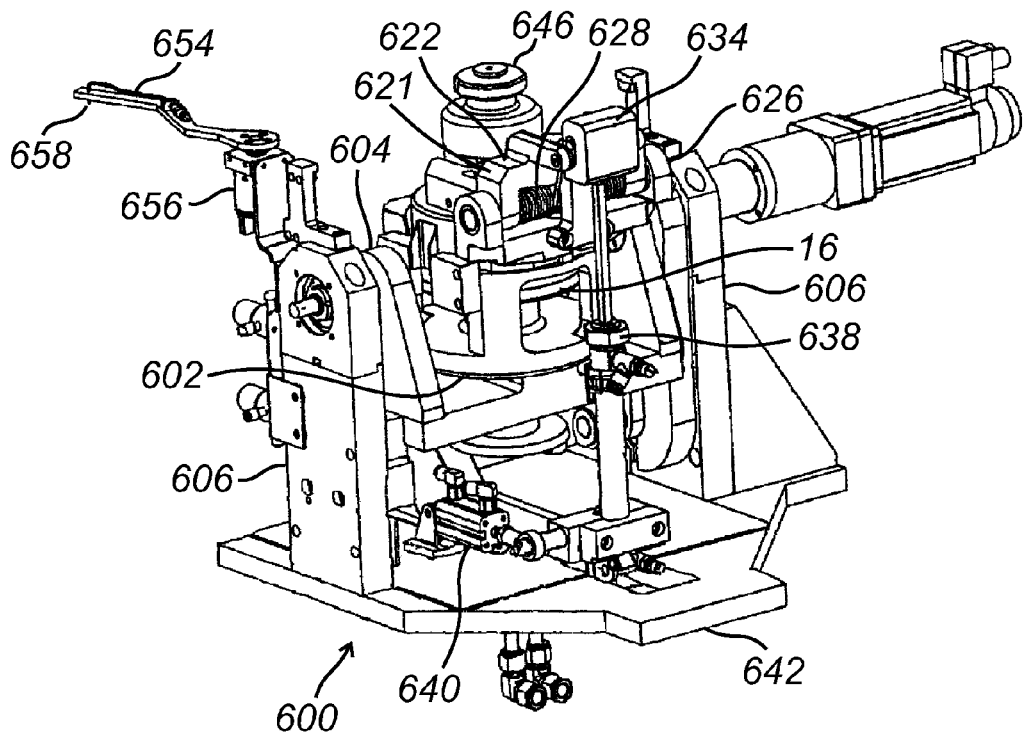
FIGS. 6a-d illustrate a preseparator recovery and collection module of the system, FIG. 6a being a perspective illustration of the module from the front and to one side, FIG. 6b being a perspective illustration of it from the rear and to one side, FIG. 6c being a highly schematic representation of a preseparator, and FIG. 6d being a highly schematic representation of a stopper assembly.
Figure 6B:
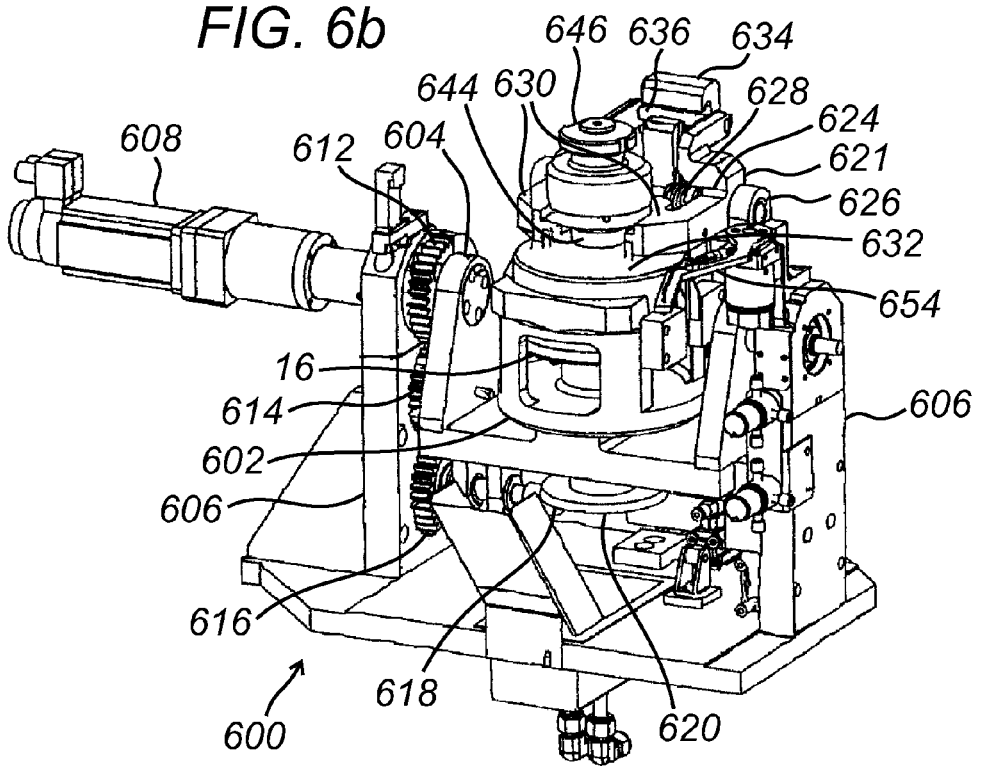
Figure 6C:
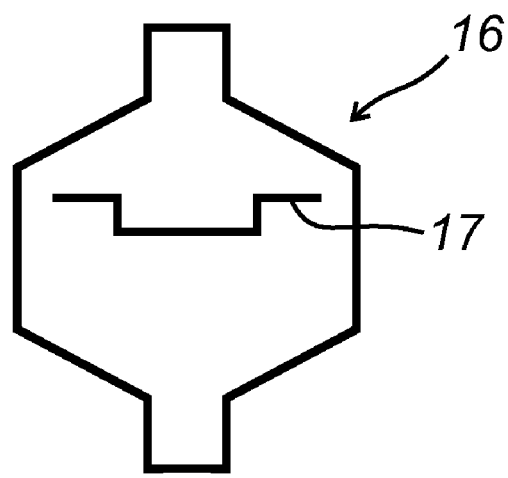
Figure 6D:
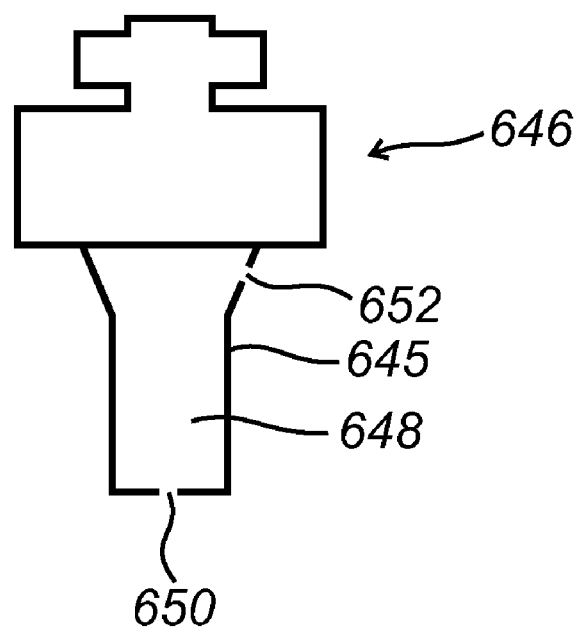

In FIG. 6b the top part of the preseparator 16 can be seen at 644. It receives, as a sealing fit and through a bayonet fitting (not shown), a stopper assembly 646 having an internal reservoir 648 (FIG. 6d). To appreciate the function of the reservoir 648, refer to FIG. 6c, which is a highly schematic representation of a preseparator 16 and shows a collection cup 17 within it. The sample solution is collected from the cup 17 using the FHR 900 (FIG. 9), and for this purpose, at the end of the recovery process, it is necessary to ensure that this collection cup 17 contains sample solution. The reservoir 648 serves to supply this. Referring to FIG. 6d, the reservoir is defined by a tubular body 645 of the stopper assembly 646 to be inserted into the preseparator 16, and is closed but for a small dispense opening 650 at its closed lower end and small vent openings 652 at its upper end. During the recovery process, after agitation has taken place to dissolve the sample material, the preseparator 16 is inverted to submerge the reservoir 648. After a sufficient period for the reservoir to fill with liquid, the preseparator is restored to an upright position, causing the liquid in the reservoir to escape through the dispense opening 650 into the collection cup 17.

Referring once more to FIGS. 6a and b, during recovery and clean up dispensing of solvent to the interior of the preseparator 16 is carried out using a preseparator dispense arm 654 which is mounted upon a rotary actuator 656 and so movable between a dispense position, in which a delivery nozzle 658 lies above the open mouth of the preseparator 16, and a safe position (shown) in which the dispense arm 654 will not foul the rotating parts during agitation.

In use, a controlled dose of solvent is introduced to the preseparator 16, which is then closed and rotated to agitate. A sample is collected using the fluid handling robot 900 (FIGS. 8a-b), and the solution is then poured into a waste chute. Clean up is carried out by solvent addition and agitation.

Component Drying Module (CDM) 700

Figure 7A:
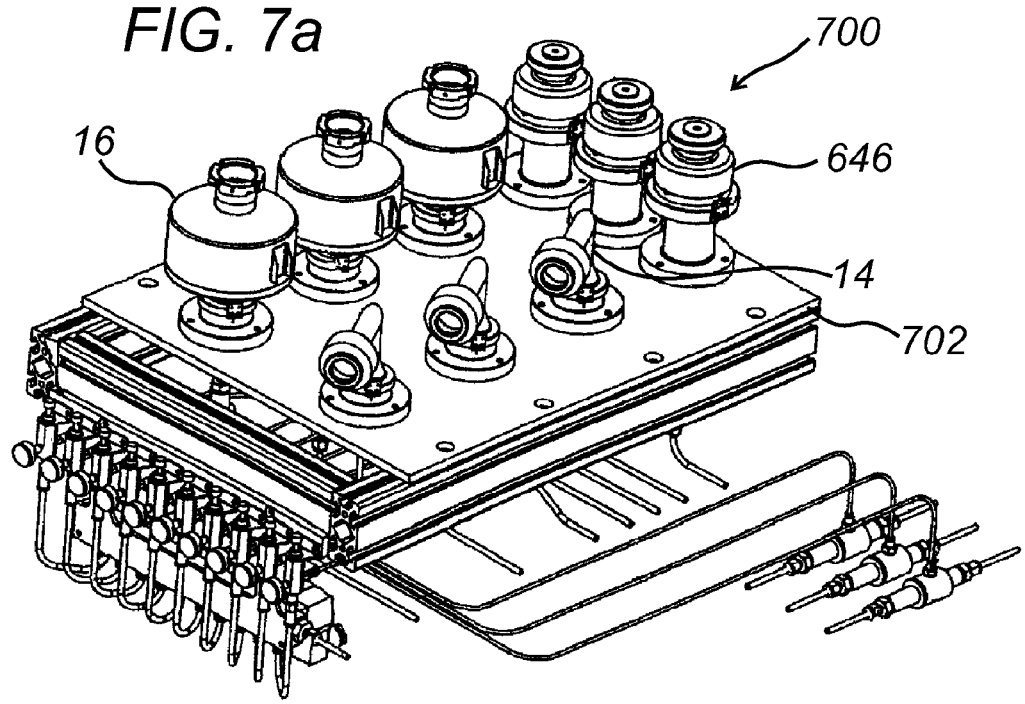
FIGS. 7a and b illustrates a component drying module of the system, FIG. 7a being a perspective illustration of the module from the front and to one side, and FIG. 7b being a further perspective illustration of it from beneath.
Figure 7B:
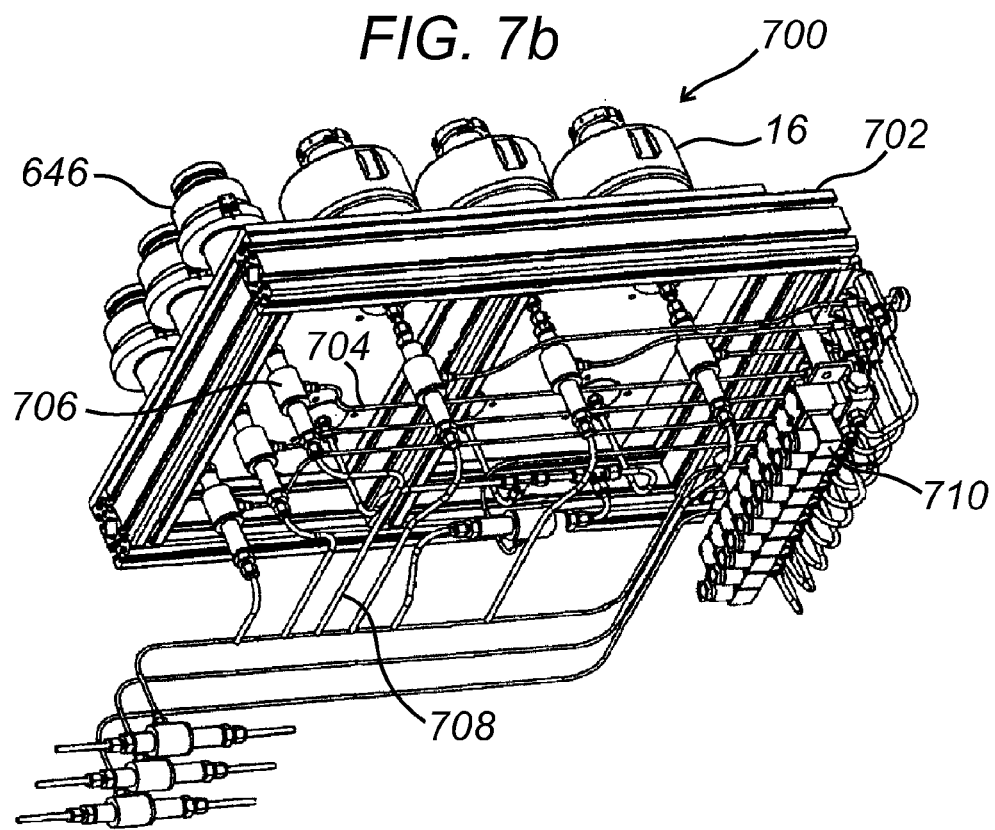

Some impactor components need to be dried and stored after the recovery and clean up processes, and this is done in the component drying module (CDM) 700 (FIGS. 7a and 7b). Note that to ensure that the system is not held up waiting for dry components to become available, the relevant impactor components are provided in triplicate. The CDM 700 carries out forced air drying of the induction ports 14, preseparators 16 and stopper assemblies 646 by drawing air through them.

A CDM base plate 702 supports the components while they are being dried. It carries a set of sealing fittings each adapted to receive one of the components 14, 16, 646 to be dried. The sealing fittings are hidden from view in the drawings by the components themselves, but each comprise a boss upon which the component seats, the boss having a through-passage for drying air. To avoid the need for a vacuum pump (as opposed to a compressor) air lines 704 leading from each sealing fitting each have a venturi device 706, of well known type, which receives compressed air through a line 708 from a valve 710 and in response creates the partial vacuum required, to draw air through the component 14, 16, 646. The valves 710 are independently controllable, and the vacuum to any given sealing fitting is switched off after the drying operation.

Nozzle Tray Wash Module (NTWM) 800

Figure 8A:
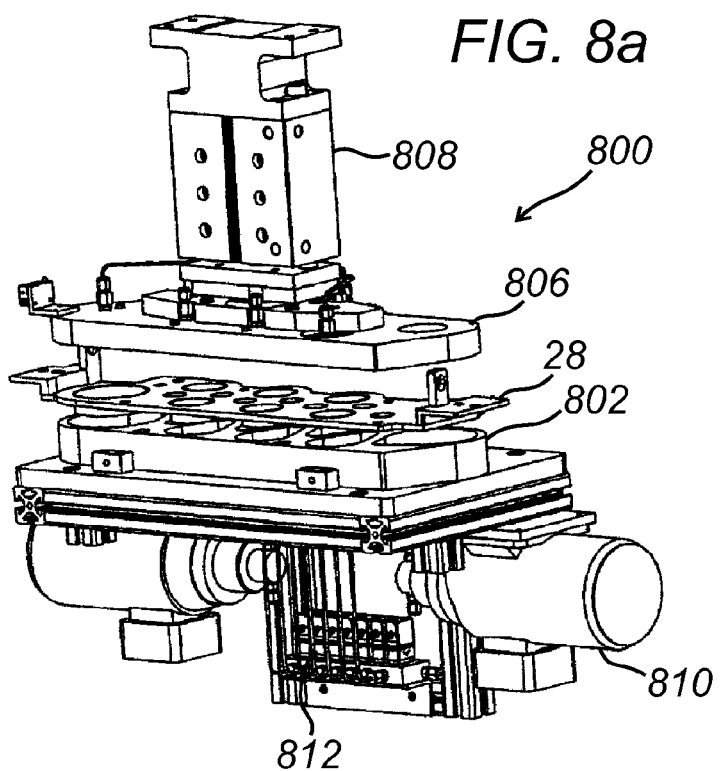
FIGS. 8a and b illustrate a nozzle tray wash unit of the system, FIG. 8a being a perspective illustration of the module from the front and to one side, and FIG. 8b being a further perspective illustration of it from the rear.
Figure 8B:
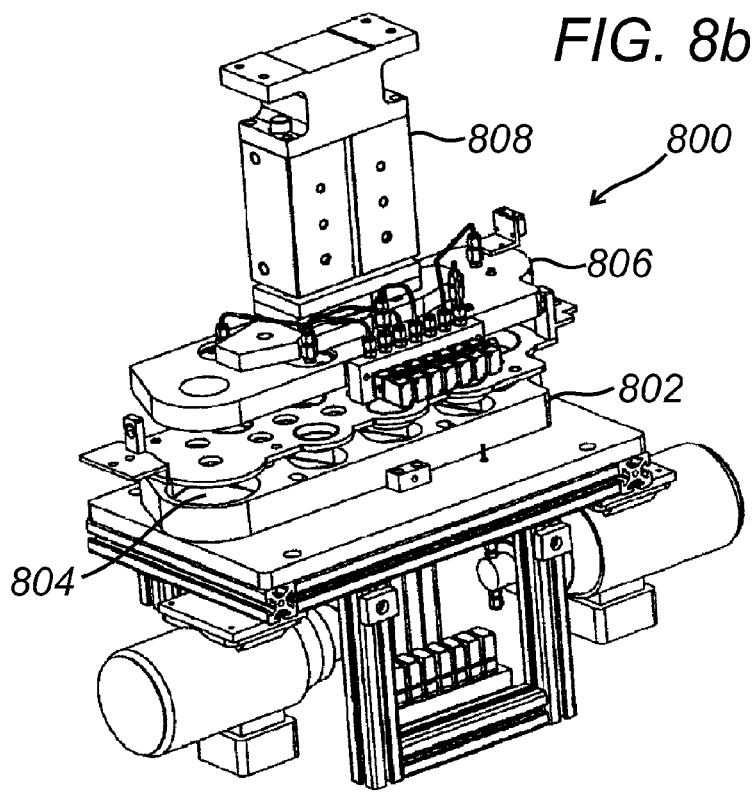

While washing of the nozzle tray 28 is not needed after every impactor dosing, it has been found that periodic washing is needed and this is carried out by the NTWM 800 shown in FIGS. 8a and 8b. The nozzle tray 28 is placed by means of the CTHS 1000 (FIG. 10) upon a lower manifold 802 of the NTWM 800 having respective depressions 804 to receive each of the nozzles 26 of the nozzle tray 28, and an upper manifold 806 is lowered into position over the nozzle tray by means of a pneumatic overhead actuator 808 on which it is mounted, so that each nozzle 26 of the nozzle tray 28 is contained in a sealed chamber formed between the upper and lower manifolds 806, 802. Solvent is then jetted through each nozzle 26 in turn by means of pumps 810 and fluid lines 812 to carry out washing. The fluid passes through the nozzles into the said sealed chambers, from which it is exhausted via outlets (not shown, but formed in the lower manifold 802). This is done for each nozzle 26 in turn, since the resistance to flow of different nozzles 26 is dramatically different.

Fluid Handling Robot (FHR) 900

The FHR 900 (FIG. 9) serves in particular to collects assay solutions for analysis from the induction port 14, the preseparator 16, and each of the cups 24. However it also performs, where necessary, subsequent dilution of the assays in preparation for their analysis, injection of the assay solutions into analysis ports, transportation of well plates used for storage of the assays, and transfer of standard solutions to the well plates.

Figure 9:
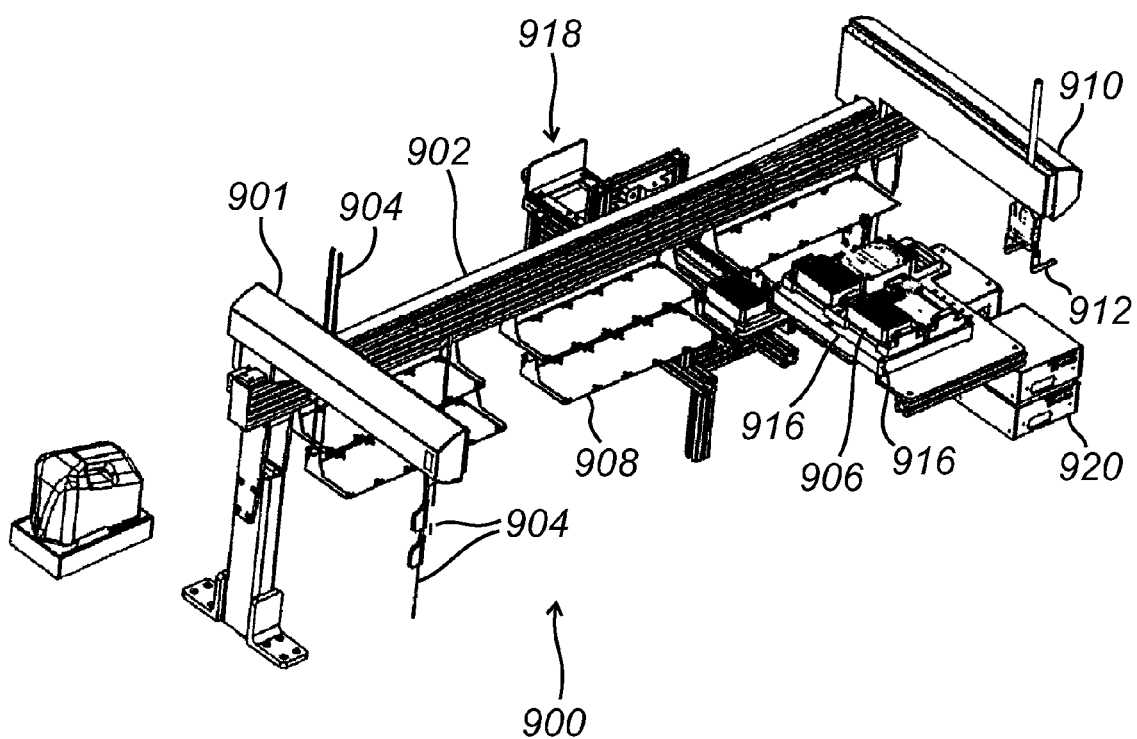
FIG. 9 is a perspective illustration of a fluid handling robot and related components of the system.

Fluid handling robots as such are well known and the FHR 900 is constructed from "off the shelf" components. FIG. 9 shows a cantilevered fluid handling arm 901 mounted for travel along the X axis upon a beam 902. Its probes 904, through which fluids are collected and exhausted, are movable along the Z axis to enable them to be inserted in the various receptacles, and are movable along the Y direction upon the arm 901. Also shown in the drawing are well plates 906 to receive the assays themselves. Assays drawn from the induction port etc are ejected into the well plates 906, and the result of a protracted run of the system will be a set of well plates 906 filled with assays for analysis. The well plates 906 are mounted on a temperature regulating device 916, which in the present embodiment is of a known type using Peltier solid state heat pumps. The well plates 906 are releasably clamped in place so that they are not moved when accessed by the FHR 900 (FIG. 9).

The FHR 900 has, in this embodiment, four probe needles 904. Thus for example during collection of samples from the cup tray 22, assays are collected from four of the cups serially using respective needles, but the discharge of these four assays to respective locations on the well plate 906 is concurrent. Filled well plates 906 are placed on any of five plate racks 908 by means of a plate handling arm 910, which again is mounted upon the beam 902 and has a gripper 912 movable along three axes, and is also able to rotate.

Washing of each probe needles 904, and its associated conduits, is achieved by inserting the probe needle in a wash pot and discharging a quantity of system fluid through it. The discharge washes internal surfaces. Fluid in the wash pot serves to wash the probe needle's external surfaces.

If a user requires access to a well plate 906, this can be achieved through an access station comprising a drawer 918. In response to a user request, the plate handling arm 910 places the chosen well plate 906 in the drawer 918, which is then released so that the user can open it and remove the well plate 906.

The analysis itself, typically by chromatographic techniques, may be carried out by a separate system to which the well plates 906 are delivered. However FIG. 9 shows an injection module to which the assays are delivered, using the FHR 900, for transfer to an "on-line" analytical instrument.

The FHR 900 can also be used to collect and discharge solvent for dilution of the assays.

Figure 1B:
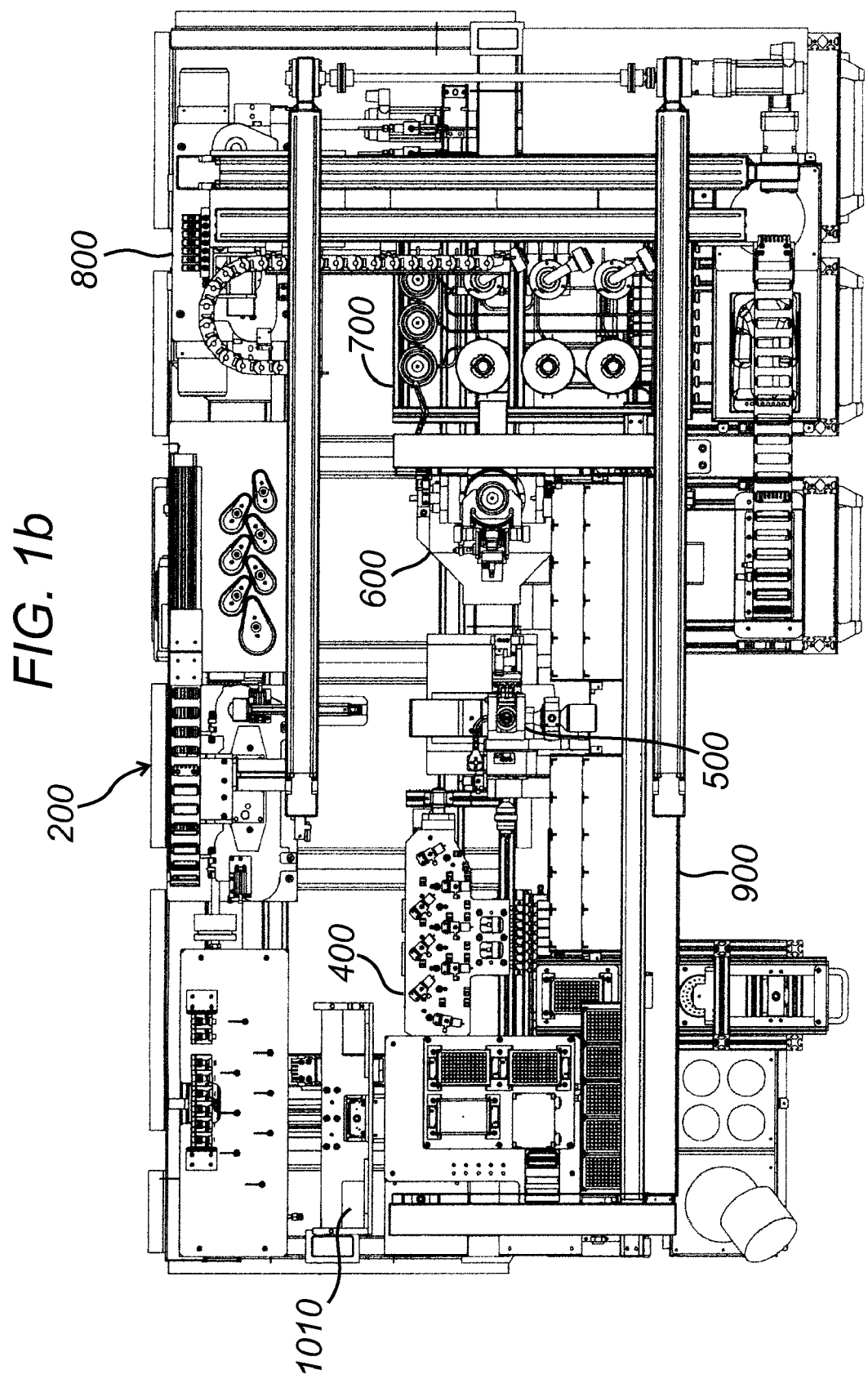
Figure 1D:
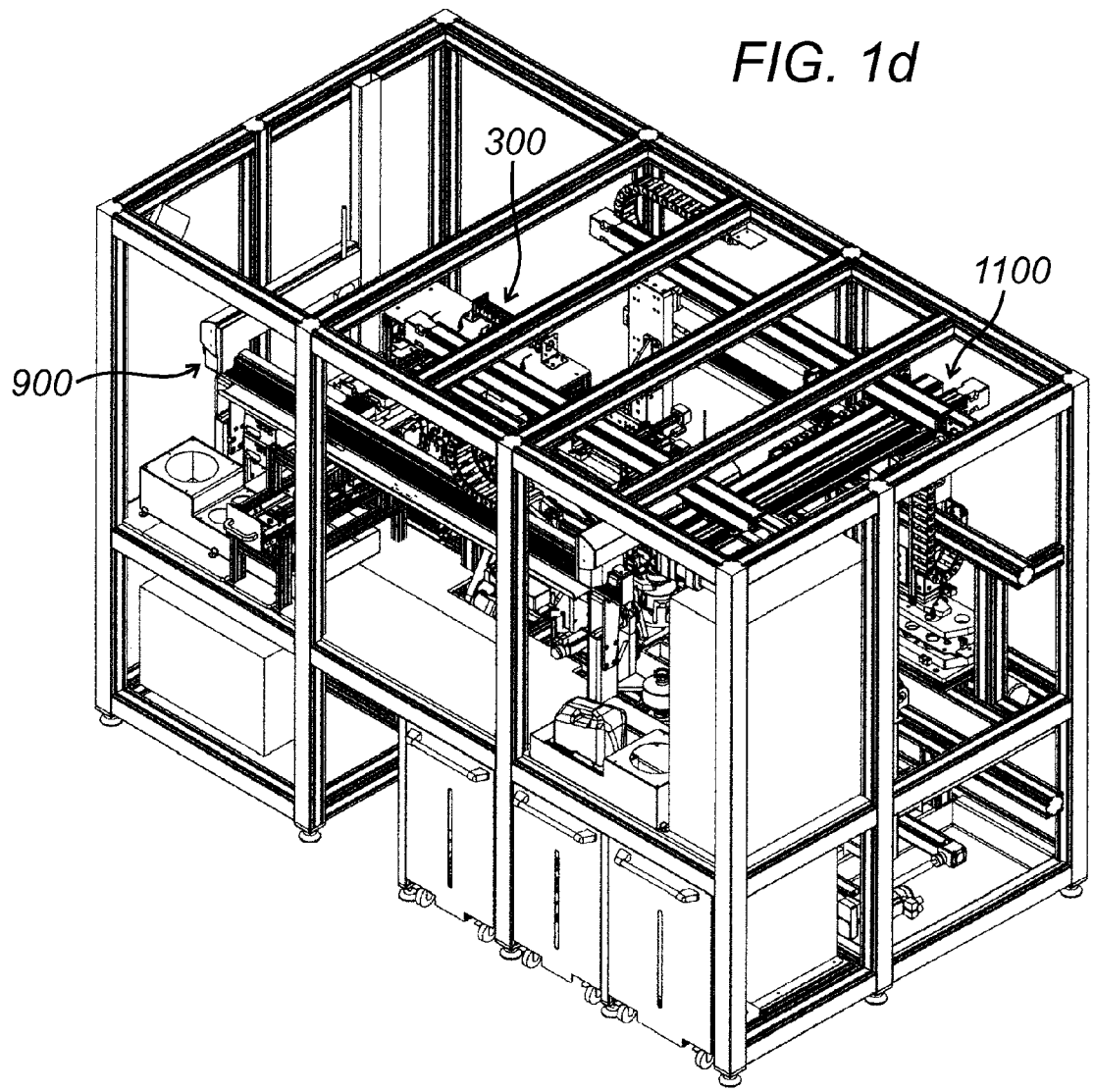

It can be seen in FIG. 1b that the FHR 900, CTRCM 400, PRCM 500 and PRCM 600 are all positioned to the same side in the system 100 to enable the FHR 900 to perform the above-described collection functions on the CTRCM 400, IPRCM 500 and PRCM 600.

Tray Handling System (THS) 1000

Figure 10:
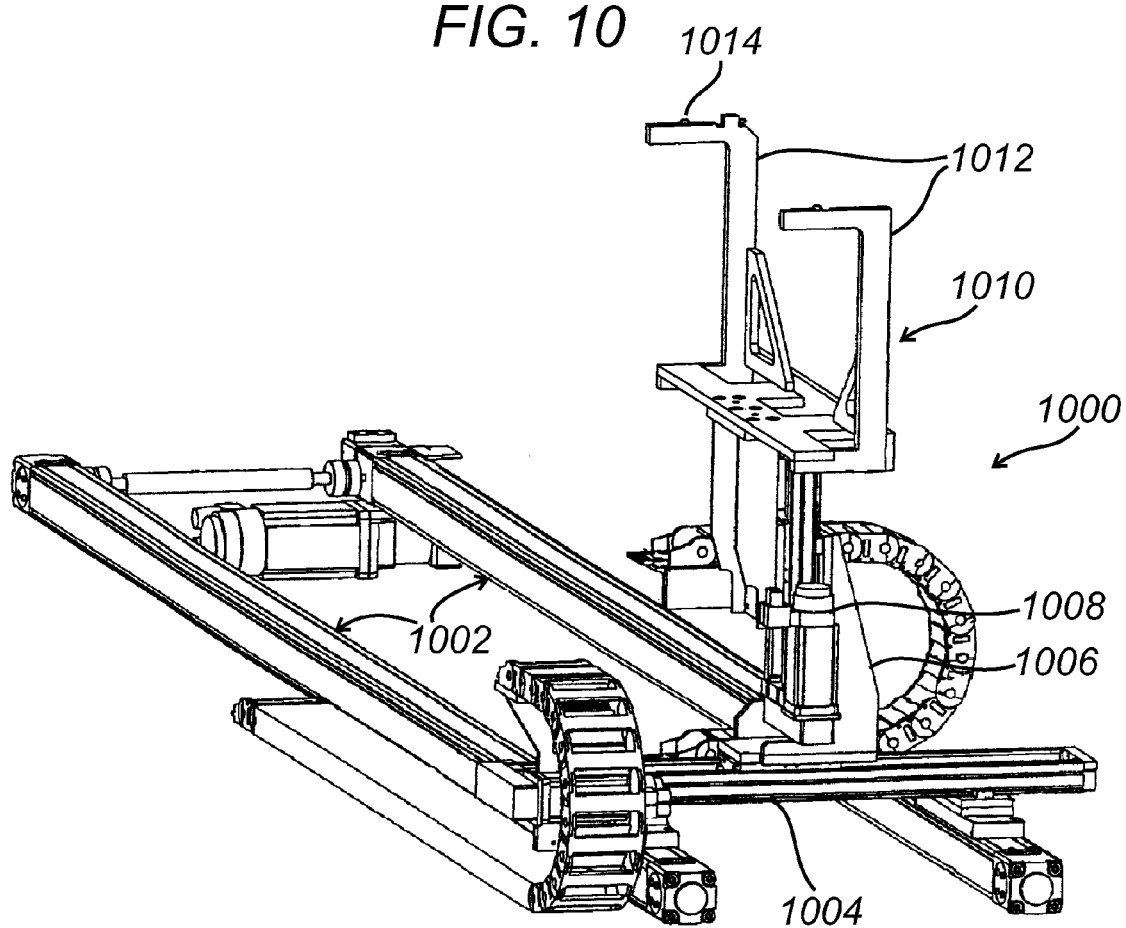
FIG. 10 is a perspective illustration of a tray handling system.

This shared system, shown in FIG. 10, is mounted at low level in the system 100 and carries out pick and place operations on the cup trays 22 and the nozzle trays 28:

from one ledge to another within the CCM 300 (for cup coating);

from the CDM 700 to the IADDM 200 (when cup coating is not required);

from the IADDM 200 to the CDM 700 (when a leak test is failed, and re-assembly of the impactor 10 is to be carried out);

from the IADDM 200 to the CTRCM 400, for recovery and clean up; and from the CTRCM 400 to the CDM 700, when secondary drying is required.

From the IADDM 200 to the NTWM 800 for nozzle tray wash.

The THS 1000 provides for motion along all three axes. It comprises a parallel pair of bed bars 1002 extending along the X axis direction and a traveler bar 1004 which is movable along the bed bars under software control. For this purpose the bed bars 1002 are formed as servo driven linear actuators, incorporating a belt drive for the traveler bar 1004. These are well known and proprietary units, and other forms of actuator could be used. Likewise the traveler bar 1004 forms a servo driven linear actuator for moving carriage 1006 along its length in the Y direction. The traveler bar 1004 supports a servo driven linear actuator 1008 which carries a top frame assembly 1010 whose upwardly projecting "C" shaped arms 1012 are adapted to receive, support and locate the cup tray 22 through projections 1014 which engage with complementary features of the cup tray 22. Lifting the cup tray 22 involves positioning the arms 1012 beneath it and raising them to engage the tray. Putting the tray down is simply the reverse process. The upstanding arms 1012 enable the cup trays to be placed within both the cup coating module 300 and the cup tray recovery and collection module 400 and the IADDM 200.

The location of the THS 1000 is difficult to appreciate from FIG. 1 as it is largely obscured, but FIG. 11b shows its position with respect to the framework of the system 100 as a whole, and to the IPPHS 1100. Also the top frame assembly 1010 of the THS 1000 is seen in FIG. 1*b*.

Induction Port and Preseparator Handling System (IPPHS) 1100

The IPPHS 1100 shown in FIGS. 11*a* to 11*c*, is mounted overhead in the system 100 and serves to move the induction ports 14:

from the CDM 700 to the IADDM 200, for assembly;
from the IADDM 200 to the CDM 700 (when a leak test is failed, and re-assembly of the impactor 10 is to be carried out);
from the IADDM 200 to the IPRCM 500, for recovery and clean up; and
from the IPRCM 500 to the CDM 700, when drying is required.

It also serves to move the preseparators 16:

from the CDM 700 to the IADDM 200, for assembly;
from the IADDM 200 to the CDM 700 (when a leak test is failed, and re-assembly of the impactor 10 is to be carried out);
from the IADDM 200 to the PRCM 600, for recovery and clean up; and
from the PRCM 600 to the CDM 700, when drying is required.

Finally it serves to move the stopper assemblies 646 from the CDM 700 to the PRCM 600.

The IPPHS 1100 engages the induction ports 14 and the preseparators 16 through a pair of shaped jaws 1102 which have three axes of translational motion—X, Y, Z—and also two axes of rotational motion—wrist (rotation of the jaws about their axis) and pitch. It comprises a parallel pair of overhead bed bars 1104 extending along the X axis direction and an overhead traveler bar 1106 movable along the overhead bed bars 1104. Again the bars 1104 form servo driven linear actuators. An overhead carriage 1108 is movable along the overhead traveler bar 1106 in the Y direction and supports an upright guide bar 1110 supporting a Z axis carriage 1112 which in its turn carries an integrated manipulation unit 1114 (FIG. 11*c*) providing for rotational (wrist and pitch) motion of the jaws 1102. The actual release/grip motion of the jaws is provided by a pneumatic actuator 1116. The jaws 1102 have opposed lower part cylindrical recesses 1118 (FIG. 11*a*) for holding the throat and preseparator, and upper part cylindrical recesses 1120 (FIG. 11*c*), whose axis is at right angles to that of the lower recesses 1118, used for gripping the stopper assembly 646. For this purpose the jaws 102 are turned through 90 degrees using the wrist articulation in order to grip the assembly 646, and rotated through 90 degrees to release the bayonet fitting.

The specific embodiments of the invention described above with reference to the accompanying Figures are by way of example only, and the scope of the present invention extends to other embodiments and variations within the scope of the appended claims.

We claim:

1. An automated system for performing repeated testing using an impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the system comprising an impaction station for performing impaction testing using the assembled impactor;
a cup manifold recovery station for recovering sample material from the impactor cups in a solvent;
an impactor head cleaning station; and
at least one handling system for assembling the impactor for impaction, and for subsequently disassembling the impactor and delivering the cup manifold and the impactor head to their respective stations.

2. A system as claimed in claim 1 further comprising a nozzle manifold cleaning station, the handling system being adapted to disassemble the nozzle manifold from the impactor head and deliver the nozzle manifold to its cleaning station.

3. A system as claimed in claim 1, comprising an impactor head handling device having a movable support for carrying the impactor head between stations and an engagement device for releasably coupling the nozzle manifold to the impactor head.

4. A system as claimed in claim 3 further comprising a nozzle manifold cleaning station and a handling system for delivering the nozzle manifold to the nozzle manifold cleaning station.

5. A system as claimed in claim 3 in which the engagement device comprises at least one movable finger for engaging a peripheral region of the nozzle manifold, to couple it to the impactor head.

6. A system as claimed in claim 1, comprising an impactor head handling device having a movable support for carrying the impactor head, the support having a first axis of motion for advancing/retracting the impactor head with respect to the cup manifold to assemble/disassemble the impactor.

7. A system as claimed in claim 6, wherein the support has a second axis of motion for moving the impactor head from one station to another.

8. A system as claimed in claim 6, in which the impactor head handling device is adapted to exert a controlled biasing force upon the impactor head, to urge it toward the cup manifold.

9. A system as claimed in claim 8, comprising an impactor head position sensor for determining when the impactor head is in an acceptable position with respect to the cup manifold.

10. A system as claimed in claim 8 in which one of the impactor head and the cup manifold has a resilient mounting for equalising pressure across the area of contact of the impactor head and the cup manifold.

11. A system as claimed in claim 8 in which the impactor head is fixedly coupled to the movable support and is separated from it by resilient spacers for equalising pressure across the area of contact of the impactor head and the cup manifold.

12. Apparatus for use in an impaction testing arrangement, the apparatus comprising an impactor which has a cup manifold defining multiple impaction cups and an impactor head defining transfer passages each communicating with a respective nozzle, so that in the assembled impactor a route is defined for through-flow via the impaction cups, the nozzles and the transfer passages, the apparatus further comprising an impactor head clean up device having an exposed contact plate provided with multiple fluid outlet apertures connected to a fluid source, the fluid outlet apertures being positioned to correspond to openings of the transfer passages in the impactor head, so that when the impactor head is presented to the contact plate, fluid is able to be output into the transfer passages to clean them.

13. Apparatus as claimed in claim 12, in which the fluid outlet apertures communicate with recess formed in the contact plate.

14. Apparatus as claimed in claim 12, in which the contact plate is provided with a mounting which prevents it from moving.

15. Apparatus for use in an impaction testing arrangement, the apparatus comprising an impactor which comprises a cup manifold defining multiple impaction cups, an impactor head defining transfer passages, and a nozzle manifold which defines multiple nozzles and is disposable between the cup manifold and the impactor head, so that in the assembled impactor a route is defined for through-flow via the impaction cups, the nozzles and the transfer passages, the apparatus further comprising a nozzle manifold wash module comprising first and second wash manifolds shaped to receive the nozzle manifold between themselves, an opening mechanism for moving the first and second wash manifolds with respect to each other between (a) an open configuration which permits the nozzle manifold to be introduced between them and (b) a closed configuration in which each nozzle is contained in a sealed enclosure defined between the first and second wash manifolds, and ports which communicate with the said sealed enclosures formed by the first and second wash manifolds in their closed configuration and which are connectable to a fluid source for passing fluid through the sealed enclosures to carry out washing of the nozzle manifold.

16. A device for cleaning and preparing an impactor preseparator having two ports for through-flow of material being tested, and an internal impaction cup which is to be at least partially filled with liquid for use, the device comprising a preseparator support structure adapted to receive and mount the preseparator and provided with a first closure for closing one of the preseparator ports;

a support mounting which provides for a tumbling motion of the support structure;

a drive for driving the tumbling motion of the support structure; and a second closure for closing the other of the preseparator ports, the second closure communicating with a fluid reservoir and having at least one opening through which the fluid reservoir communicates, when the second closure is used to close the said preseparator port, with the interior of the preseparator, so that by means of the said drive, the preseparator is movable between (a) an inverted position in which the fluid reservoir is filled with fluid from the interior of the preseparator and (b) an upright position in which fluid is released from the fluid reservoir through the said opening into the internal impaction cup.

17. A device as claimed in claim 16 further comprising a fluid outlet for dispensing fluid into the preseparator.

18. A device as claimed in claim 16, in which the second closure incorporates the fluid reservoir.

\* \* \* \* \*